(12) United States Patent
Salvatore et al.

(10) Patent No.: US 7,598,403 B2
(45) Date of Patent: Oct. 6, 2009

(54) SYNTHESIS OF CHROMANONES

(75) Inventors: Brian A. Salvatore, Shreveport, LA (US); Ferdinand C. Solis, Lexington, SC (US)

(73) Assignee: The University of South Carolina Research Foundation, Columbia, SC (US)

( * ) Notice: Subject to any disclaimer, the term of this patent is extended or adjusted under 35 U.S.C. 154(b) by 7 days.

(21) Appl. No.: 10/557,065

(22) PCT Filed: May 17, 2004

(86) PCT No.: PCT/US2004/015418

§ 371 (c)(1),
(2), (4) Date: Feb. 27, 2007

(87) PCT Pub. No.: WO2004/103985

PCT Pub. Date: Dec. 2, 2004

(65) Prior Publication Data

US 2007/0203214 A1    Aug. 30, 2007

Related U.S. Application Data

(60) Provisional application No. 60/560,208, filed on Apr. 7, 2004, provisional application No. 60/471,267, filed on May 16, 2003.

(51) Int. Cl.
*C07D 311/00*    (2006.01)
(52) U.S. Cl. ...................... 549/401; 549/403
(58) Field of Classification Search ............... 549/401, 549/403
See application file for complete search history.

(56) References Cited

FOREIGN PATENT DOCUMENTS

JP        63290849      11/1988
WO     WO 99/26622 A   6/1999

OTHER PUBLICATIONS

Pathre et al. (STN Accession No. 1986:568536; Document No. 105:168536, Abstract of Canadian Journal of Chemistry (1986), 64(7), 1308-11).*
Xie et. al. (STN Accession No. 1991:602867; Document No. 115: 115:202867, Abstract of Journal of Natural Products (1991), 54(4), 1165-7).*
Xie et. al. (STN Accession No. 1995:436973; Document No. 115: 122:234945, Abstract of Journal of Natural Products (1995), 58(1), 124-7).*
Folkman, Angiogenesis in cancer, vascular, rheumatoid and other disease, Nature Medicine, 1(1):27-30 (1995).
Folkman, Anti-angiogenesis: New concept for therapy of solid tumors, Ann. Surg., 175(3):409-416 (1972).
Kosynkin et al., Benzyltriethylammonium dichloroiodate/sodium bicarbonate combination as an inexpensive, environmentally friendly, and mild Iodinating reagent for anilines, Organic Letters, 3(7):991-992 (2001).
Jackson et al., Carbonylative Coupling of an Amino Acid-derived Organozinc Reagent with Functionalized Aryl Iodides: Synthesis of Kynurenine, J. Chem. Soc., Chem. Commun., p. 2207-2208 (1995).
Jackson et al., Carbonylative coupline of organozinc reagents in the presence and absence of aryl iodides: synthesis of unsymmetrical and symmetrical ketones, J. Chem. Soc., Perkin Trans. 1:865-870 (1997).
Kabbe, Eine einfache synthese von 4-chromanonen, Synthesis, 12:886-887 (1978).
Sun et al., The first regiospecific synthesis of 8,8-dimethyl-2H,8H-pyrano[2,3-h]quinolin-2-one and related compounds, Synthesis, 11:1249-1251 (1997).
Hulme et al., A Flexible and efficient synthesis of the pyrrolidine α-glycosidase inhibitor 1,4-dideoxy-1,4-imino-D-arabinitol (DAB-1), J. Chem. Soc., Perkin Trans. 1:1837-1841 (2000).
Walser et al., Fusarium-induced osteochondrosis (tibial dyschondroplasia) in chickens, Vet. Pathol., 19(5):544-550 (1982).
Minervini et al., Immunomodulatory effects of fusarochromanones TDP-1 and TDP-2, Natural Toxins, 1:15-18 (1992).
Pawlosky et al., Mass spectral analysis and fragment ion structure of fusarochromanone, Biological Mass Spectrometry, 20:743-749 (1991).
Jackson et al., A new direct method for the synthesis of enantiomerically pure protected α-amino acids, J. Chem. Soc., Chem. Commun., 644-645 (1989).
Dunn et al., Preparation of a serine-derived organozinc reagent in tetrahydrofuran: Synthesis of novel, enantiomerically pure allenic, acetylenic and heteroaryl amino acids, Synlett, 1993, 499-500.
Dexter et al., Room temperature palladium-catalysed coupling of amino acid-derived organozinc reagents with aryl triflates, Tetrahedron, 56:4539-4540 (2000).
Pathre et al., The structure of fusarochromanone: new mycotoxin from *Fusarium roseum*, "Graminearum", Can. J. Chem., 64:1308-1311 (1986).
Lee et al., TDP-1, a toxic component causing tibial dyschondroplasia in broiler chickens, and trichothecenes from *Fusarium roseum* 'Graminearum', Applied and Environmental Microbiology, 50(1): 102-107 (1985).
Spiegel et al., Use of Nonaqueous Solvents in Parenteral Products, Journal of Pharmaceutical Sciences, 52(10): 917-927 (1963).

* cited by examiner

*Primary Examiner*—D. Margaret Seaman
*Assistant Examiner*—Nizal S Chandrakumar
(74) *Attorney, Agent, or Firm*—Senniger Powers LLP

(57) ABSTRACT

Processes for the preparation of biologically active chromanones are disclosed, including processes for the preparation of intermediates useful in the preparation of the biologically active chromanones. The chromanones and the intermediates disclosed herein may be useful for a variety of therapies, including the treatment of various cancers and the treatment of inflammation and inflammation related disorders.

17 Claims, No Drawings

SYNTHESIS OF CHROMANONES

REFERENCE TO RELATED APPLICATIONS

This application is a National Stage application based on Serial No. PCT/US04/015418 filed May 17, 2004 which is an application claiming the benefit under 35 USC 119(e) of Ser. No. 60/560,208 filed Apr. 7, 2004 and 60/471,267 filed May 16, 2003.

This invention was made with Government support under South Carolina Biomedical Research Infrastructure Network/South Carolina Experimental Program to Stimulate Competitive Research (SC-BRIN/SC EPSCoR) CRP Grant #13020 FA-21. The Government has certain rights in the invention.

BACKGROUND OF THE INVENTION

The present application is generally directed to a process for the synthesis of fusarochromanone (FC) and analogs thereof, as well as certain intermediates useful in such syntheses.

Members of the *Fusarium* species are distributed worldwide as soil inhabitants and parasites of cultivated plants. Some isolates of the species are capable of producing mycotoxins, the ingestion of which has been associated with a variety of animal intoxications. For example, chicks fed diets containing a 5% level of crude fungus cultures from *Fusarium equiseti* develop a syndrome known as Avian Tibial Dyschondroplasia (ATD), characterized by bone deformation and failure of cartilage calcification (Walser et al., 1982, Vet Pathol 19: 544-550).

Fusarochromanone ("FC") is a water soluble component derived from *Fusarium* cultures. Fusarochromanone has been purified and characterized (Pathre et al., 1986, Can. J. Chem 64: 1308-1311), and one form of this compound, designated FC101 and having the chemical formula 5-amino-2,2-dimethyl-6-[3'-(R,S)amino-4'-hydroxy-butan-1-one]-2,3-dihydro-4H-1-benzopyran-4-one, has been shown to cause ATD when administered to day-old broiler chicks (Lee et al., 1985, Appl. Environ. Microbiol. 50:102-107).

Fusarochromanone is a biologically active compound; it is an inhibitor of angiogenesis, which is the development of new blood vessels from existing capillaries. Certain angiogenesis inhibitors have been suggested for use in therapies for cancer, rheumatoid arthritis, psoriasis, Kaposi's Sarcoma, ischemic heart disease, atherosclerosis and ocular diseases, such as diabetic retinopathy, involving retinal vessel proliferation.

SUMMARY OF THE INVENTION

Among the various aspects of the present invention are synthetic processes for the preparation of FC101 and the analogs thereof, as well as certain intermediates or starting materials which may be used in such synthetic schemes.

Briefly, therefore, the present invention is directed to chromanones useful in the preparation of FC101 and the analogs thereof corresponding to Formula 21:

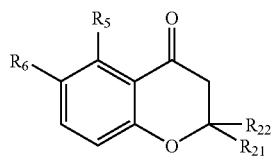

wherein $R_5$ is amino or nitro;

$R_6$ is amino, hydroxy, halo, perfluorinated sulfonic ester, $R_{61}C(O)$—, $R_{62}C(O)O$—, $R_{61}C(O)NH$—, $R_{62}CHCH$— or $R_{62}CC$—;

$R_{21}$ and $R_{22}$ are independently hydrogen, alkyl, or aryl;

$R_{61}$ and $R_{62}$ are hydrogen, hydrocarbyl, substituted hydrocarbyl, heterocyclo, alkoxy, heterocyclooxy, amino, or halo.

The present invention is also directed to processes for the synthesis of starting materials and intermediates falling within the scope of Formula 21.

Other objects and features of this invention will be in part apparent and in part pointed out hereinafter.

DETAILED DESCRIPTION OF THE PREFERRED EMBODIMENTS

In general, the present invention is directed to chromanones corresponding to Formula 21 and to synthetic processes for their preparation:

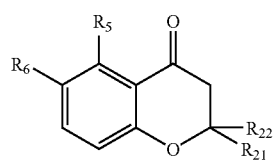

wherein $R_5$ is amino or nitro;

$R_6$ is amino, hydroxy, halo, perfluorinated sulfonic ester, $R_{61}C(O)$—, $R_{62}C(O)O$—, $R_{61}C(O)NH$—, $R_{62}CHCH$— or $R_{62}CC$—;

$R_{21}$ and $R_{22}$ are independently hydrogen, alkyl, or aryl;

$R_{61}$ and $R_{62}$ is hydrogen, hydrocarbyl, substituted hydrocarbyl, heterocyclo, alkoxy, heterocyclooxy, amino, or halo.

In accordance with the present invention, $R_6$ may represent a range of substituents. For example, $R_6$ may be a relatively small moiety such as —$NH_2$, —OH, or halo. Alternatively, $R_6$ may be a somewhat larger moiety such as a perfluorinated sulfonic ester, $R_{61}C(O)$—, $R_{62}C(O)O$—, $R_{61}C(O)NH$—, $R_{62}CHCH$— or $R_{62}CC$—. For example, in one embodiment, $R_6$ is $R_{61}C(O)$— or $R_{61}C(O)NH$— and $R_{61}$ is hydrogen, substituted hydrocarbyl, heterocyclo, amino, alkoxy, heterocyclooxy, or halo, preferably substituted hydrocarbyl.

Advantageously, chromanones corresponding to Formula 21 may be used in the synthesis of FC101 (chromanone 21 wherein $R_5$ is —$NH_2$; $R_6$ is $R_{61}C(O)$; $R_{21}$ and $R_{22}$ are each methyl; and $R_{61}$ is $HOCH_2CH(NH_2)CH_2$—). Alternatively, chromanones corresponding to Formula 21 may be used to synthesize analogs of FC101 which may themselves be biologically active, or may be used as part of a drug-discovery process to determine structure-activity relationships for chromanones, generally, in connection with various biological processes or targets; such analogs, for example, would have an $R_{21}$ or $R_{22}$ substituent other than methyl, or an $R_6$ substituent other than $HOCH_2CH(NH_2)CH_2C(O)$—.

An intermediate chromanone which may be used in the synthesis of FC101 and the analogs thereof corresponds to Formula 22:

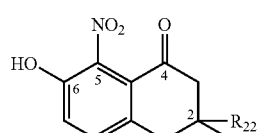

wherein $R_{21}$ and $R_{22}$ are independently hydrogen, alkyl, or aryl. In one embodiment, $R_{21}$ and $R_{22}$ are independently hydrogen or alkyl; for example, $R_{21}$ and $R_{22}$ may independently be methyl, ethyl, propyl, butyl or pentyl. Alternatively, one of $R_{21}$ and $R_{22}$ may be hydrogen and the other may be aryl, e.g., phenyl.

Chromanone 22 may be prepared, for example, by nitration of the corresponding 6-hydroxy-chroman-4-one (i.e., a chromanone corresponding to chromanone 22 except for the C5 nitro group), chromanone 20:

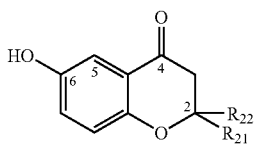

20

The starting material, i.e., chromanone 20 may be prepared as described, for example, in Example 2 and then nitrated, for example, using potassium nitrate and sulfuric acid in a polar solvent.

Chromanone 22 may be used as a substrate for the synthesis of a variety of other chromanones. For example, chromanone 22 may be used as a substrate for the synthesis of chromanone 32:

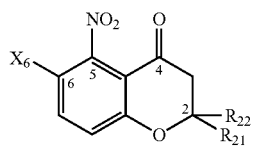

32 wherein $X_6$ is perfluorinated sulfonic ester; and $R_{21}$ and $R_{22}$ are independently hydrogen, alkyl, or aryl. In another preferred embodiment, $X_6$ is a perfluorinated sulfonic ester moiety such as triflate or nonaflate and $R_{21}$ and $R_{22}$ are independently hydrogen or alkyl; for example, $R_{21}$ and $R_{22}$ may independently be methyl, ethyl, propyl, butyl or pentyl. Alternatively, $X_6$ may be a perfluorinated sulfonic ester moiety, one of $R_{21}$ and $R_{22}$ may be hydrogen and the other may be aryl, e.g., phenyl. Chromanone 32 may be derived from chromanone 22 by treating chromanone 22 with the appropriate anhydride. For example, to prepare the C6 triflate or nonaflate, chromanone 22 may be treated with triflate anhydride or nonaflate anhydride, respectively.

Chromanone 22 may also be used as a substrate for the synthesis of chromanone 27:

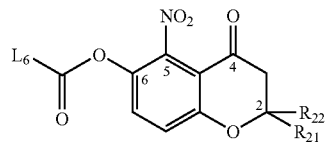

27 wherein $L_6$ is chloro or imidazoyl; and $R_{21}$ and $R_{22}$ are independently hydrogen, alkyl, or aryl. In another preferred embodiment, $L_6$ is chloro or imidazoyl and $R_{21}$ and $R_{22}$ are independently hydrogen or alkyl; for example, $R_{21}$ and $R_{22}$ may independently be methyl, ethyl, propyl, butyl or pentyl. Alternatively, $L_6$ may be chloro or imidazoyl, one of $R_{21}$ and $R_{22}$ may be hydrogen and the other may be aryl, e.g., phenyl. Chromanone 27 may be derived from chromanone 22 by treating chromanone 22 with an appropriate reagent; for example, phosgene, diphosgene or carbonyl diimidazole.

Chromanones 27 and 32 may, in turn, be used as a substrate for the preparation of other chromanones. For example, chromanone 32 may be used as a substrate for the synthesis of chromanone 42:

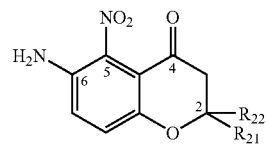

42 wherein $R_{21}$ and $R_{22}$ are independently hydrogen, alkyl, or aryl. In one preferred embodiment, $R_{21}$ and $R_{22}$ are independently hydrogen or alkyl; for example, $R_2$, and $R_{22}$ may independently be methyl, ethyl, propyl, butyl or pentyl. Alternatively, one of $R_{21}$ and $R_{22}$ may be hydrogen and the other may be aryl, e.g., phenyl. Chromanone 42 may be derived from chromanone 32 by treating chromanone 32 with ammonia in the presence of a palladium catalyst. For example, chromanone 32 may be treated with ammonia in the presence of $[Pd_2(dba)_3]$, a phosphine compound and a base; for example, the base can be an aqueous base, particularly, a metal alkoxide and water, potassium carbonate and the like. Chromanone 42 is produced upon heating and may be isolated conventionally.

Chromanone 32 may also be used as a substrate for the synthesis of chromanone 52:

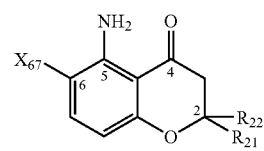

52 wherein $X_{67}$ is halo; and $R_{21}$ and $R_{22}$ are independently hydrogen, alkyl, or aryl. In one preferred embodiment, $R_{21}$ and $R_{22}$ are independently hydrogen or alkyl; for example, $R_{21}$ and $R_{22}$ may independently be methyl, ethyl, propyl, butyl or pentyl. Alternatively, one of $R_{21}$ and $R_{22}$ may be hydrogen and the other may be aryl, e.g., phenyl. Chromanone 52 may be derived from chromanone 32 by a reduction reaction followed by an aromatic halogenation reaction. For example, chromanone 32 may be reduced by contact with hydrogen gas in the presence of a palladium catalyst (particularly palladium on carbon) in the presence of an amine (e.g. trialkylamine) and an alcohol (e.g. ethanol). Subsequently, a halogenating reagent is contacted with the reduced compound to produce chromanone 52. An exemplary halogenating reagent is benzyltriethyl ammonium dichloroiodate, which is prepared in Example 10.

An exemplary synthesis of chromanone 52 is depicted in the following reaction scheme and begins with the conversion of chromanone 32 (wherein $X_6$ is, for example triflate or nonaflate) to chromanone 33 by reaction with hydrogen in the presence of a palladium catalyst and triethylamine. Chromanone 33 in turn, is converted to chromanone 52-I (chromanone 52 wherein $X_{67}$ is iodo) by reaction with benzyltriethylammonium dichloroidodide in the presence of $NaHCO_3$.

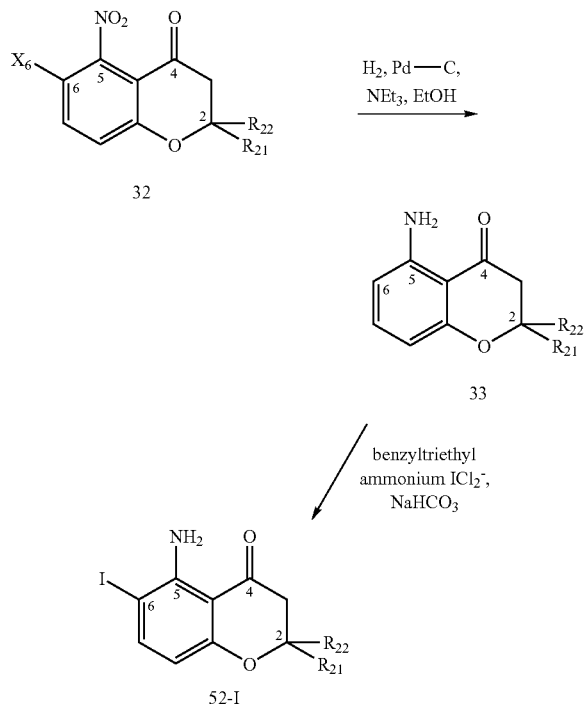

Chromanone 42 may also be used as a substrate for the synthesis of chromanone 47:

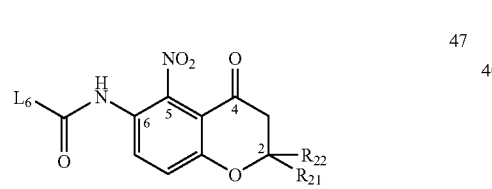

wherein $L_6$ is chloro or imidazoyl; and $R_{21}$ and $R_{22}$ are independently hydrogen, alkyl, or aryl. In another preferred embodiment, $R_{21}$ and $R_{22}$ are independently hydrogen or alkyl; for example, $R_{21}$ and $R_{22}$ may independently be methyl, ethyl, propyl, butyl or pentyl. Alternatively, one of $R_{21}$ and $R_{22}$ may be hydrogen and the other may be aryl, e.g., phenyl. Chromanone 47 may be derived from chromanone 42 by treating chromanone 42 with an appropriate reagent; for example, phosgene, diphosgene or carbonyl diimidazole.

Chromanone 42 may be used as a substrate for the preparation of chromanone 43:

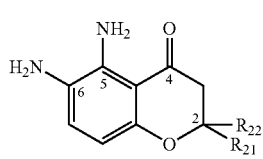

Chromanone 43 may be produced from chromanone 42 by protecting the C6 amino group, reducing the C5 nitrate group, followed by deprotection of the C6 amino group.

Chromanones 32 and 52 may be also used as substrates for the synthesis of chromanone 62:

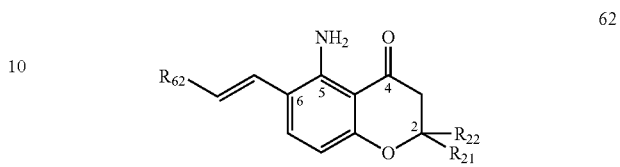

wherein $R_{62}$ is hydrogen, hydrocarbyl, substituted hydrocarbyl, heterocyclo, alkoxy, heterocyclooxy, amino or halo; and $R_{21}$ and $R_{22}$ are independently hydrogen, alkyl, or aryl. In one preferred embodiment, $R_{62}$ is substituted alkyl and $R_{21}$ and $R_{22}$ are independently hydrogen or alkyl; for example, $R_{21}$ and $R_{22}$ may independently be methyl, ethyl, propyl, butyl or pentyl. Alternatively, one of $R_{21}$ and $R_{22}$ may be hydrogen and the other may be aryl, e.g., phenyl. In another preferred embodiment, $R_{62}$ is $P_{66}OCH_2CH(NP_{67}P_{68})CH_2C(O)$— wherein $P_{66}$, $P_{67}$ and $P_{68}$ are independently hydrogen or a protecting group. Chromanone 62 may be derived from chromanones 32 and 52 by reaction with alkene, $R_{62}CHCH_2$, mediated by a $Pd^{2+}$ reagent, a trialkyl or triaryl phosphine and potassium carbonate. The $Pd^{2+}$ reagent can be $PdCl_2$, $Pd(OAc)_2$, $PdBr_2$ or $PdI_2$. The trialkyl or triaryl phosphine can be tributylphosphine, tricyclohexylphosphine or triphenylphosphine.

Chromanones 32 and 52 may also be used as a substrate for the synthesis of chromanone 67:

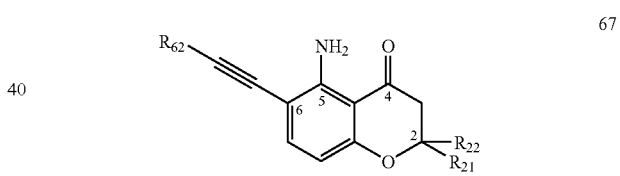

wherein $R_{62}$ is hydrogen, hydrocarbyl, substituted hydrocarbyl, heterocyclo, alkoxy, heterocyclooxy, amino or halo; and $R_{21}$ and $R_{22}$ are independently hydrogen, alkyl, or aryl. In one preferred embodiment, $R_{62}$ is substituted alkyl and $R_{21}$ and $R_{22}$ are independently hydrogen or alkyl; for example, $R_{21}$ and $R_{22}$ may independently be methyl, ethyl, propyl, butyl or pentyl. Alternatively, one of $R_{21}$ and $R_{22}$ may be hydrogen and the other may be aryl, e.g., phenyl. In another preferred embodiment, $R_{62}$ is $P_{66}OCH_2CH(NP_{67}P_{68})CH_2C(O)$— wherein $P_{66}$, $P_{67}$ and $P_{68}$ are independently hydrogen or a protecting group. Chromanone 67 may be derived from chromanone 32 and chromanone 52 by treating with an alkyne, a $Cu^+$ ion, $Pd(PPh_3)_4$ and a tertiary alkyl amine. The $R_{61}$ substituent of the alkyne, $R_{62}CCH$, has the reactive functional groups protected. The reaction takes place in a polar aprotic solvent; exemplary solvents are tetrahydrofuran, dimethylformamide, dioxane, and the like. The $Cu^+$ ion can be provided by CuCl, CuI, CuSCN, and the like. The tertiary alkyl amine used as a base in the reaction can be triethylamine, tripropylamine, tributylamine, triisopropylamine, diisopropylethylamine, tripentylamine, trihexylamine, tricyclohexylamine, and the like.

Chromanone 22 may also be converted to chromanone 24 by reduction of the C5 nitro group.

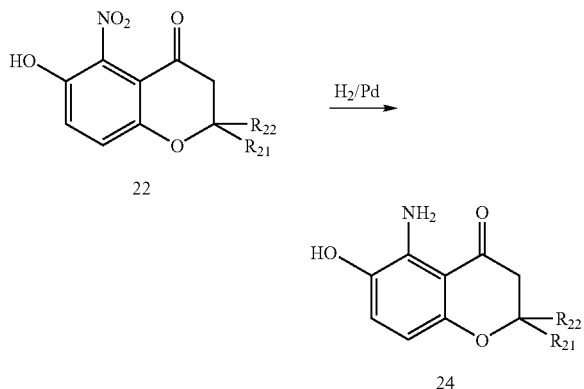

A range of compounds may be derived from the intermediates described above. Exemplary compounds can be synthesized by the following synthetic schemes.

mation involves a primary or secondary amine, e.g. $R_{61}R_{62}NH$, and a base wherein $R_{61}$ and $R_{62}$ are as previously defined. The reactive functional groups present in the substituents $R_{61}$ and $R_{62}$ of the primary or secondary amine, $R_{61}R_{62}NH$, are protected during reaction with the acyl chloride chromanone 111. Once the primary or secondary amine, $R_{61}R_{62}NH$, has reacted to form the urea chromanone 112, the groups protecting the reactive functional groups of $R_{61}$ and $R_{62}$ can be removed by methods known in the art.

Step 3 involves the conversion of acyl chloride 111 into carbamate chromanone 113. This transformation involves an alcohol, e.g. $R_{61}OH$, and a base wherein $R_{61}$ is as previously defined. The reactive functional groups present in substituent $R_{61}$ of the alcohol are protected during the reaction with acyl chloride chromanone 111. Once the alcohol, $R_{61}OH$, has reacted to form carbamate chromanone 113, the groups protecting the reactive functional groups of $R_{61}$ can be removed by methods known in the art. The base used in steps 2 and 3 is a base that is capable of reacting with excess protons produced during the reaction of the amine or alcohol with acyl chloride chromanone 111. For example, tertiary amines,

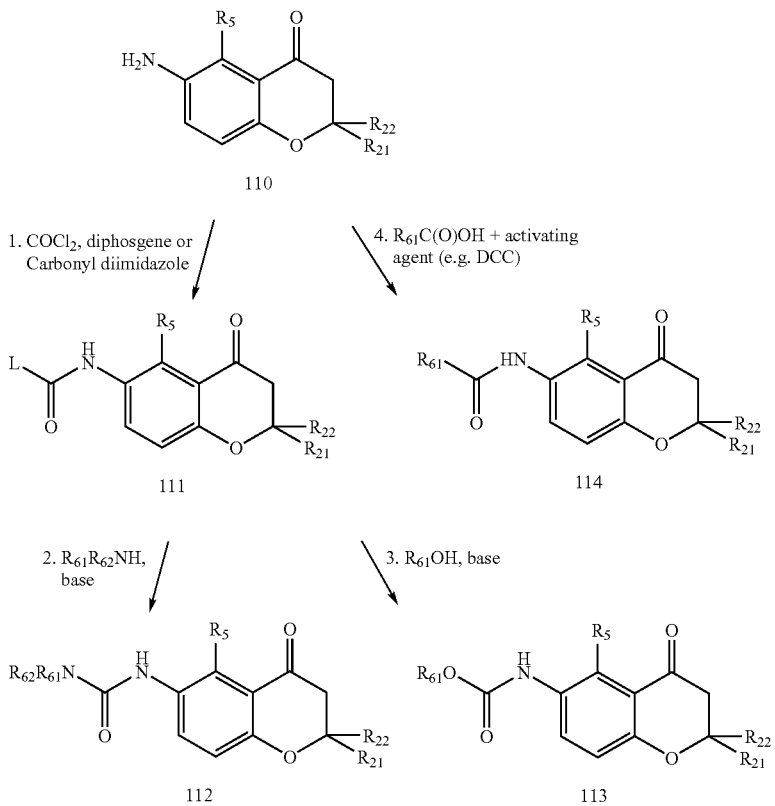

In reaction scheme 1, $R_5$ is amino, protected amino or nitro; $R_{21}$ and $R_{22}$ are independently hydrogen, alkyl or aryl; $R_{61}$ and $R_{62}$ are independently hydrogen, hydrocarbyl, substituted hydrocarbyl or heterocyclo; and L is chloro or imidazoyl. In step 1, C6 amino chromanone 110 is converted to chromanone 111 using an appropriate reagent; for example, phosgene, diphosgene or carbonyl diimidazole or an equivalent reagent can be used. Step 2 involves the conversion of acyl chloride 111 into urea chromanone 112. This transforalkali metal carbonates or alkaline earth metal carbonates are useful bases for this reaction. In one embodiment, preferably, the base used in steps 2 and 3 is a tertiary amine, particularly pyridine, triethylamine or diisopropylethylamine.

Step 4 involves the conversion of C6 amino chromanone 110 to amide chromanone 114. For this conversion to proceed, an activated carboxylic acid is reacted with C6 amino chromanone 110. The carboxylic acid used in step 4 is represented by $R_{61}C(O)OH$, wherein $R_{61}$ is as previously defined. The reactive functional groups present in substituent $R_{61}$ of the carboxylic acid are protected during the reaction with C6 amino chromanone 110. Once the carboxylic acid, $R_{61}C(O)OH$, has reacted to form amide chromanone 114, the groups protecting the reactive functional groups of $R_{61}$ can be removed by methods known in the art. The activating agent used in step 4 can be an agent capable of activating a carboxylic acid; for example, dicyclohexyl carbodiimide, diisopropylcarbodiimide, diethyl cyanophosphonate, diphenylphosphorylazide, uronium salts and phosphonium salts. In one embodiment, the activating agent used in step 4 is dicyclohexylcarbodiimide (DCC).

alcohol, e.g. $R_{61}OH$, and a base wherein $R_{61}$ is as previously defined. The reactive functional groups present in substituent $R_{61}$ of the alcohol are protected during the reaction with acyl chloride chromanone 121. Once the alcohol, $R_{61}OH$, has reacted to form carbonate chromanone 123, the groups protecting the reactive functional groups of $R_{61}$ can be removed by methods known in the art. The base used in steps 2 and 3 is a base that is capable of reacting with excess protons produced during the reaction of the amine or alcohol with acyl chloride chromanone 121. For example, tertiary amines, alkali metal carbonates or alkaline earth metal carbonates are useful bases for this reaction. In one embodiment, preferably,

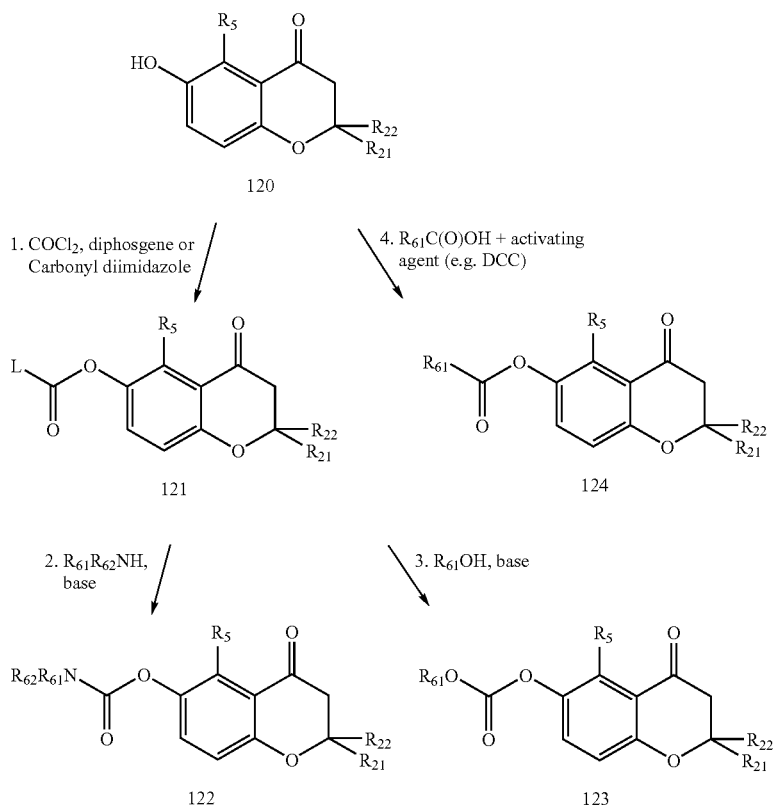

Reaction Scheme 2

In reaction scheme 2, $R_5$ is amino, protected amino or nitro; $R_{21}$ and $R_{22}$ are independently hydrogen, alkyl or aryl; $R_{61}$ and $R_{62}$ are independently hydrogen, hydrocarbyl, substituted hydrocarbyl or heterocyclo; and L is chloro or imidazoyl. In step 1, chromanone 120 is converted to chromanone 121 using an appropriate reagent; for example, phosgene, diphosgene or carbonyl diimidazole or an equivalent reagent can be used. Step 2 involves the conversion of acyl chloride 121 into carbamate chromanone 122. This transformation involves a primary or secondary amine, e.g. $R_{61}R_{62}NH$, and a base wherein $R_{61}$ and $R_{62}$ are as previously defined. The reactive functional groups present in the substituents $R_{61}$ and $R_{62}$ of the primary or secondary amine, $R_{61}R_{62}NH$, are protected during reaction with acyl chloride chromanone 121. Once the primary or secondary amine, $R_{61}R_{62}NH$, has reacted to form carbamate chromanone 122, the groups protecting the reactive functional groups of $R_{61}$ and $R_{62}$ can be removed by methods known in the art.

Step 3 involves the conversion of acyl chloride 121 into carbonate chromanone 123. This transformation involves an the base used in steps 2 and 3 is a tertiary amine, particularly pyridine, triethylamine or diisopropylethylamine.

Step 4 involves the conversion of C6 hydroxy chromanone 120 to ester chromanone 124. For this conversion to proceed, an activated carboxylic acid is reacted with C6 hydroxy chromanone 120. The carboxylic acid used in step 4 is represented by $R_{61}C(O)OH$, wherein $R_{61}$ is as previously defined. The reactive functional groups present in substituent $R_{61}$ of the carboxylic acid are protected during reaction with C6 hydroxy chromanone 120. Once the carboxylic acid, $R_{61}C(O)OH$, has reacted to form amide chromanone 124, the groups protecting the reactive functional groups of $R_{61}$ can be removed by methods known in the art. The activating agent used in step 4 can be an agent capable of activating a carboxylic acid; for example, dicyclohexyl carbodiimide, diisopropylcarbodiimide, diethyl cyanophosphonate, diphenylphosphorylazide, uronium salts and phosphonium salts. In one embodiment, the activating agent used in step 4 is dicyclohexylcarbodiimide (DCC).

Reaction Scheme 3

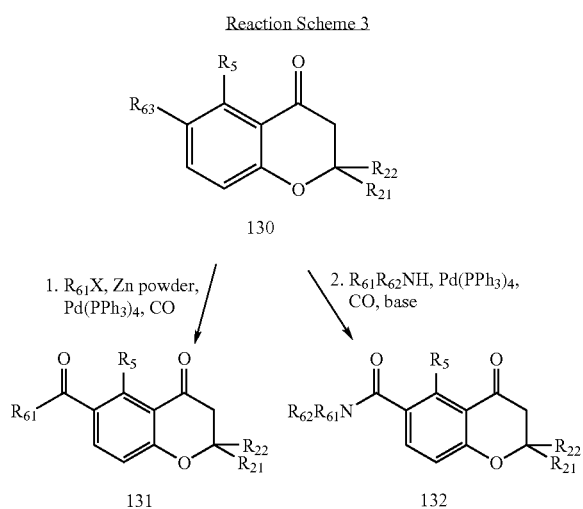

130

131

132

In reaction scheme 3, $R_5$ is amino, protected amino or nitro; $R_{21}$ and $R_{22}$ are independently hydrogen, alkyl, or aryl; $R_{61}$ and $R_{62}$ are independently hydrogen, hydrocarbyl, substituted hydrocarbyl or heterocyclo; and $R_{63}$ is halo or perfluorinated sulfonic ester. In one preferred embodiment, $R_{63}$ is iodide, triflate or nonaflate. In step 1, chromanone 130 is converted to ketone chromanone 131 by reaction with alkyl halide, $R_{61}X$, wherein X is a halide, Zn powder, $Pd(PPh_3)_4$ and carbon monoxide. Optionally, activating agent(s) can be added to the reaction mixture to activate the Zn. For example, 1,2-dibromoethane and trimethylsilyl chloride (TMSCl) or iodine can chemically activate Zn, whereas sonication of Zn provides physical activation. The reactive functional groups present in substituent $R_{61}$ of the alkyl halide are protected during reaction with chromanone 130. Once the alkyl halide, $R_{61}X$, has reacted to form ketone chromanone 131, the groups protecting the reactive functional groups of $R_{61}$ can be removed by methods known in the art.

Step 2 involves conversion of chromanone 130 into amide chromanone 132. This conversion involves reaction of chromanone 130 with a primary or secondary amine, $R_{61}R_{62}NH$, $Pd(PPh_3)_4$, carbon monoxide and base. The reactive functional groups present in the substituents $R_{61}$ and $R_{62}$ of the primary or secondary amine, $R_{61}R_{62}NH$, are protected during reaction with chromanone 130. Once the primary or secondary amine, $R_{61}R_{62}NH$, has reacted to form amide chromanone 132, the groups protecting the reactive functional groups of $R_{61}$ and $R_{62}$ can be removed by methods known in the art.

Reaction Scheme 4

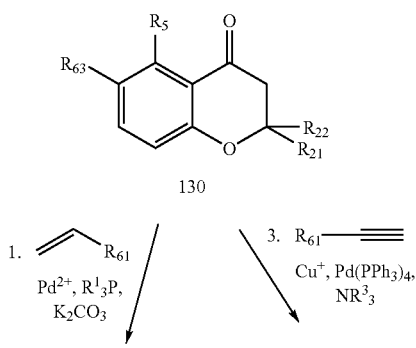

130

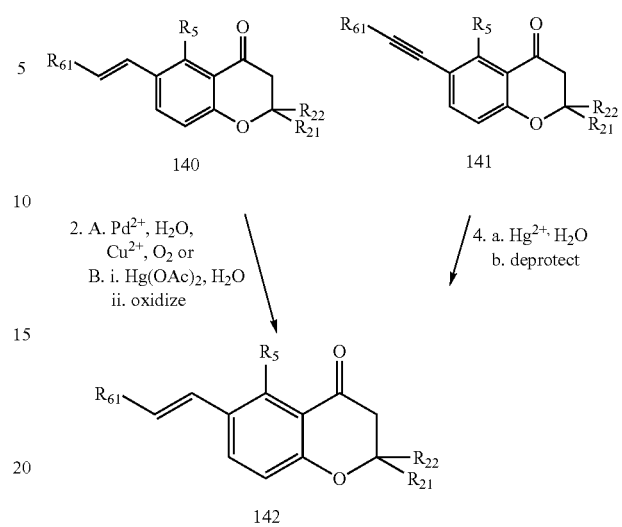

140

141

142

In reaction scheme 4, $R_5$ is amino, protected amino or nitro; $R_{21}$ and $R_{22}$ are independently hydrogen, alkyl or aryl; $R_{61}$ and $R_{62}$ are independently hydrogen, hydrocarbyl, substituted hydrocarbyl or heterocyclo; $R_{63}$ is halo or perfluorinated sulfonic ester. In one preferred embodiment, $R_{63}$ is iodide, triflate or nonaflate; $R^1$ is alkyl or aryl; and $R^3$ is alkyl. In step 1, chromanone 130 is converted to chromanone 140 by reaction with an alkene, $R_{61}CHCH_2$, mediated by a $Pd^{2+}$ reagent, a trialkyl or triaryl phosphine and potassium carbonate. The $Pd^{2+}$ reagent can be $PdCl_2$, $Pd(OAc)_2$, $PdBr_2$ or $PdI_2$. The trialkyl or triaryl phosphine can be tributylphosphine, tricyclohexylphosphine or triphenylphosphine. This reaction is usually sterically controlled, thus the bite angle of the phosphine influences the reactivity, wherein the larger the bite angle, the more strain on the alkene ligand and the greater the reactivity of the Pd-alkene complex.

In step 2, chromanone 140 is transformed into ketone chromanone 142 under one of two alternate sets of reaction conditions. First, under conditions for step 2A, the conversion occurs by a Wacker process. The Wacker process involves a $Pd^{2+}$ reagent, water, a $Cu^{2+}$ reagent and oxygen. The $Pd^{2+}$ reagent, usually $PdCl_2$, is reduced during the reaction to Pd and the alkene is oxidized to produce the ketone. The $Cu^{2+}$ reagent oxidizes the Pd to $Pd^{2+}$ to reduce the amount of Pd necessary to effect the reaction. The resulting $Cu^+$ ions are oxidized to $Cu^{2+}$ by air.

Alternately, chromanone 140 is converted to ketone chromanone 142 under conditions wherein the first step is addition of water mediated by $Hg(OAc)_2$, followed by oxidation. The oxidizing agent can be an oxidizing agent that effects the desired oxidation of the hydroxy group to a keto group without oxidizing the rest of the molecule. For example, the oxidizing agent can be pyridinium chlorochromate (PCC), a Swern reagent, a chromium reagent, chromic acid, $K_2Cr_2O_7$ and the like.

Both of the alternate reaction conditions in step 2 produce a Markovnikov product. This is due to the preference of the hydrogen for the regular secondary carbon of the alkene (not the benzylic secondary carbon), thus producing a benzylic carbocation and subsequently the keto group is formed in the benzylic position as well.

Step 3 involves the reaction of chromanone 130 to form alkyne chromanone 141. This reaction involves an alkyne, a $Cu^+$ ion, $Pd(PPh_3)_4$ and a tertiary alkyl amine. The $R_{61}$ substituent of the alkyne, $R_{61}CCH$, has the reactive functional groups protected. The reaction takes place in a polar aprotic solvent; exemplary solvents are tetrahydrofuran, dimethylformamide, dioxane, and the like. The $Cu^+$ ion can be provided by CuCl, CuI, $Cu_2O$, $Cu_2S$, $Cu_2Te$, CuSCN, and the like. The tertiary alkyl amine used as a base in the reaction can be triethylamine, tripropylamine, tributylamine, triisopropylamine, diisopropylethylamine, tripentylamine, trihexylamine, tricyclohexylamine, and the like.

Step 4 involves the reaction of alkyne chromanone 141 to form ketone chromanone 142. This reaction takes place by an overall addition of water across the triple bond. The reagents used to effect the conversion are water and an $Hg^{2+}$ salt. The $Hg^{2+}$ salt can be $Hg(OAc)_2$, $HgSO_4$, HgO, $HgBr_2$, $HgCl_2$, $HgI_2$, $Hg(NO_3)_2$, HgS, HgTe, $Hg(SCN)_2$, and the like. Optionally, $H_2SO_4$ can be added to effect the addition of water across the triple bond, however, consideration of the reactivity of the protecting groups used in the molecule will determine whether $H_2SO_4$ addition would be beneficial. After addition of water, suitable reagents to deprotect reactive functional groups of $R_5$ or $R_{61}$ are added to the reaction mixture to produce ketone chromanone 142.

Chromanones of formula 21 of the instant invention are useful for a variety of pharmaceutical therapies in mammals including humans and are preferably administered in the form of a pharmaceutical composition comprising an effective therapeutic amount of a compound of the instant invention in combination with at least one pharmaceutically or pharmacologically acceptable carrier. The carrier, also known in the art as an excipient, vehicle, auxiliary, adjuvant, or diluent, is any substance which is pharmaceutically inert, confers a suitable consistency or form to the composition, and does not diminish the therapeutic efficacy of the compounds. The carrier is "pharmaceutically or pharmacologically acceptable" if it does not produce an adverse, allergic or other untoward reaction when administered to a mammal or human, as appropriate.

The pharmaceutical compositions containing the therapeutic compounds of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular therapeutic compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Naim, in: *Remington's Pharmaceutical Science* (A. Gennaro, ed.), Mack Publishing Co., Easton, Pa., (1985), pp. 1492-1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

The compositions of the invention for oral administration comprise an effective therapeutic amount of a compound of the invention in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption.

The therapeutic compounds of the present invention are also preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective therapeutic amount of the therapeutic compound in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., $\alpha$-glycerol formal, $\beta$-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-($\beta$-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$ poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.) (Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia* 24, *The National Formulary* 19, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917-927 (1963).

Preferred solvents include those known to stabilize the therapeutic compounds, such as oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor® EL solution or Cremophor® RH 40 solution). Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®. Ethanol is a preferred solvent for use in dissolving the therapeutic compound to form solutions, emulsions, and the like.

Additional minor components can be included in the compositions of the invention for a variety of purposes well known in the pharmaceutical industry. These components will for the most part impart properties which enhance retention of the therapeutic compound at the site of administration, protect the stability of the composition, control the pH, facilitate processing of the therapeutic compound into pharmaceutical formulations, and the like. Preferably, each of these components is individually present in less than about 15 weight % of the total composition, more preferably less than about 5 weight %, and most preferably less than about 0.5 weight % of the total composition. Some components, such as fillers or diluents, can constitute up to 90 wt. % of the total composition, as is well known in the formulation art. Such additives include cryoprotective agents for preventing reprecipitation of the chromanone, surface active, wetting or emulsifying agents (e.g., lecithin, polysorbate-80, Tween® 80, pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, crosslinked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage form administration by these routes may be continuous or intermittent, depending, for example, upon the patient's physiological condition, whether the purpose of the administration is therapeutic or prophylactic, and other factors known to and assessable by a skilled practitioner.

Dosage and regimens for the administration of the pharmaceutical compositions of the invention can be readily determined by those with ordinary skill in treating cancer. It is understood that the dosage of the therapeutic compounds will be dependent upon the age, sex, health, and weight of the recipient, kind of concurrent treatment, if any, frequency of treatment, and the nature of the effect desired. For any mode of administration, the actual amount of therapeutic compound delivered, as well as the dosing schedule necessary to achieve the advantageous effects described herein, will also depend, in part, on such factors as the bioavailability of the therapeutic compound, the disorder being treated, the desired therapeutic dose, and other factors that will be apparent to those of skill in the art. The dose administered to an animal, particularly a human, in the context of the present invention should be sufficient to effect the desired therapeutic response in the animal over a reasonable period of time. Preferably, an effective amount of the therapeutic compound, whether administered orally or by another route, is any amount which would result in a desired therapeutic response when administered by that route. Preferably, the compositions for oral administration are prepared in such a way that a single dose in one or more oral preparations contains at least 20 mg of the therapeutic compound per $m^2$ of patient body surface area, or at least 50, 100, 150, 200, 300, 400, or 500 mg of the therapeutic compound per $m^2$ of patient body surface area, wherein the average body surface area for a human is 1.8 $m^2$. Preferably, a single dose of a composition for oral administration contains from about 20 to about 600 mg of the therapeutic compound per $m^2$ of patient body surface area, more preferably from about 25 to about 400 mg/$m^2$ even more preferably, from about 40 to about 300 mg/$m^2$, and even more preferably from about 50 to about 200 mg/$m^2$. Preferably, the compositions for parenteral administration are prepared in such a way that a single dose contains at least 20 mg of the therapeutic compound per $m^2$ of patient body surface area, or at least 40, 50, 100, 150, 200, 300, 400, or 500 mg of the therapeutic compound per $m^2$ of patient body surface area. Preferably, a single dose in one or more parenteral preparations contains from about 20 to about 500 mg of the therapeutic compound per $m^2$ of patient body surface area, more preferably from about 40 to about 400 mg/$m^2$ and even more preferably, from about 60 to about 350 mg/$m^2$. However, the dosage may vary depending on the dosing schedule which can be adjusted as necessary to achieve the desired therapeutic effect. It should be noted that the ranges of effective doses provided herein are not intended to limit the invention and represent preferred dose ranges. The most preferred dosage will be tailored to the individual subject, as is understood and determinable by one of ordinary skill in the art without undue experimentation.

The concentration of the therapeutic compound in a liquid pharmaceutical composition is preferably between about 0.01 mg and about 10 mg per ml of the composition, more preferably between about 0.1 mg and about 7 mg per ml, even more preferably between about 0.5 mg and about 5 mg per ml, and most preferably between about 1.5 mg and about 4 mg per ml. Relatively low concentrations are generally preferred because the therapeutic compound is most soluble in the solution at low concentrations. The concentration of the therapeutic compound in a solid pharmaceutical composition for oral administration is preferably between about 5 weight % and about 50 weight %, based on the total weight of the composition, more preferably between about 8 weight % and about 40 weight %, and most preferably between about 10 weight % and about 30 weight %.

In one embodiment, solutions for oral administration are prepared by dissolving an therapeutic compound in any pharmaceutically acceptable solvent capable of dissolving the compound (e.g., ethanol or methylene chloride) to form a solution. An appropriate volume of a carrier which is a solution, such as Cremophor® EL solution, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving an therapeutic compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as Cremophor® EL solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving an therapeutic compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsion, is added to the solution while stirring to form a pharmaceutically acceptable emulsion for parenteral administration to a patient. If desired, such emulsions can be formulated to contain a minimal amount of, or to be free of, ethanol or Cremophor® solution, which are known in the art to cause adverse physiological effects when administered at certain concentrations in parenteral formulations.

Solutions for parenteral administration can be prepared by dissolving an therapeutic compound in any pharmaceutically acceptable solvent capable of dissolving the compound (e.g., ethanol or methylene chloride) to form a solution. An appropriate volume of a carrier which is a solution, such as Cremophor® solution, is added to the solution while stirring to form a pharmaceutically acceptable solution for parenteral administration to a patient. If desired, such solutions can be formulated to contain a minimal amount of, or to be free of, ethanol or Cremophor® solution, which are known in the art to cause adverse physiological effects when administered at certain concentrations in parenteral formulations.

If desired, the emulsions or solutions described above for oral or parenteral administration can be packaged in IV bags, vials or other conventional containers in concentrated form and diluted with any pharmaceutically acceptable liquid, such as saline, to form an acceptable chromanone concentration prior to use as is known in the art.

DEFINITIONS

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, pentyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, pentenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, pentynyl, hexynyl, and the like.

The term "amino" as used herein alone or as part of another group shall denote a primary, secondary or tertiary amine which may optionally be hydrocarbyl, substituted hydrocarbyl or heteroatom substituted. Specifically included are secondary or tertiary amine nitrogens which are members of a heterocyclic ring. Also specifically included, for example, are secondary or tertiary amino groups substituted by an acyl moiety.

The term "aromatic" as used herein alone or as part of another group denote optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "carboxylic acid" refers to a RC(O)OH compound where R can be hydrogen, or substituted or unsubstituted alkyl, alkenyl, alkynyl, aryl, substituted aryl. Exemplary carboxylic acids are formic acid, acetic acid, ethanoic acid, propionic acid, and the like.

The terms "halogen" or "halo" as used herein alone or as part of another group refer to chlorine, bromine, fluorine, and iodine.

The term "halide" refers to fluoride, chloride, bromide, or iodide ions.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, acyl, acyloxy, amino, amido, nitro, cyano, ketals, acetals, esters and ethers.

The following examples illustrate the invention.

EXAMPLES

Example 1

Synthesis of Fusarochromanone

Scheme 10: Synthesis of Fusarochromanone (1)

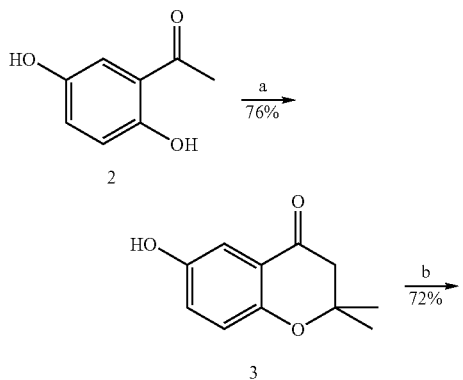

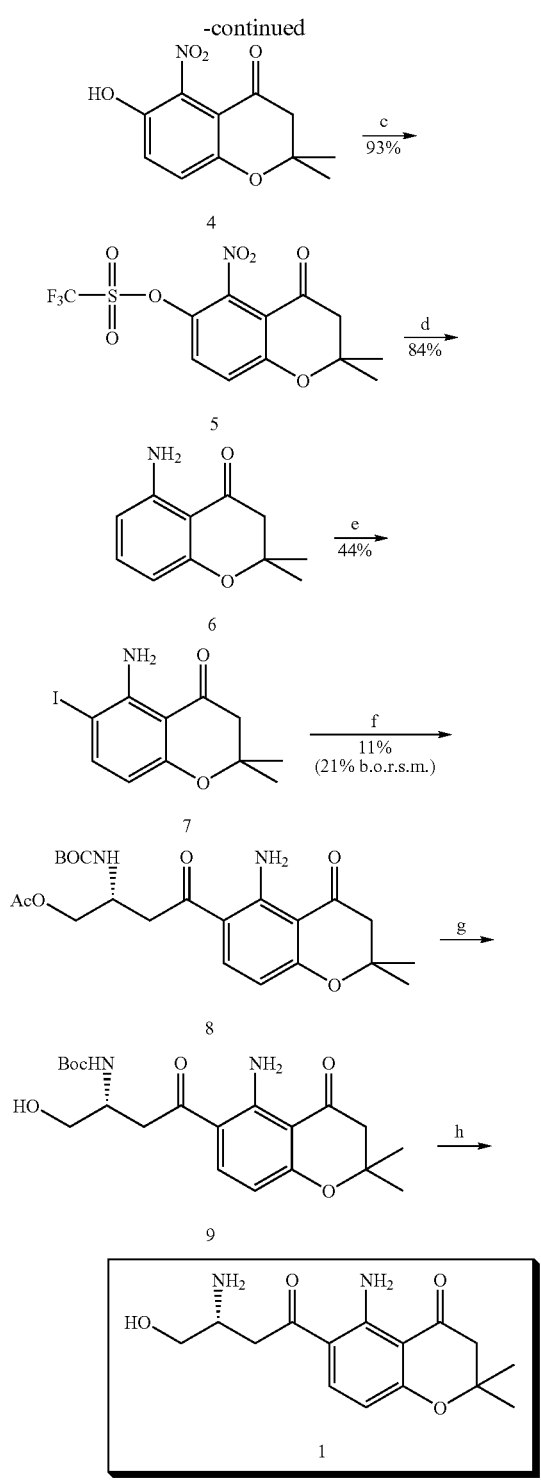

a) acetone, piperidine, pyridine, reflux. b) KNO₃, H₂SO₄, AcOH/H₂O, 10° C. c) triflic anhydride, NEt₃, CH₂Cl₂, 0° C. d) H₂, 10% Pd—C, NEt, EtOH, 50 psi, rt. e) 11 (Scheme 2), NaHCO₃, 1:1 CH₂Cl₂/MeOH, 40° C. f) 13 (Scheme 3), Zn powder, 1,2-dibromoethane, TMSCl then Pd(PPh₃)₄, CO, THF, 45° C. g) NH₃, MeOH, 0° C. h) trifluoroacetic acid/acetic acid (1:1), rt.

The regioselectivity observed in the nitration of 3, which bears a C(6) hydroxyl group, is analogous to a literature example for a chromanone with a C(6) acetamido substituent.[10] However, we could not achieve regioselective nitration when the C(6) substituent was either bromo or methyl (Scheme 11). These latter substrates reacted very slowly, with poor yields and selectivity.

Scheme 11: Summary of Regiospecific C(5) Nitration Results

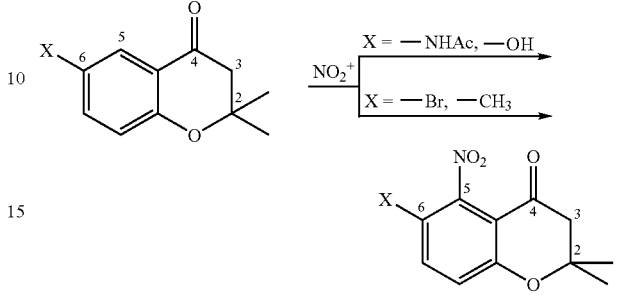

We converted the nitrochromanone (4, Scheme 10) to its corresponding triflate ester (5), which was subsequently reduced to 6 via catalytic hydrogenation. Monoiodination of 6 with a suitable reagent then provided 7. We have tried two different iodination reagents: (a) commercially available iodine chloride, and (b) benzyltriethylammonium dichloroiodate (11, Scheme 12), which we prepared ourselves.

The reaction of 6 with iodine monochloride gives 7a as the major product, regardless of the reaction conditions. In contrast, the reaction of 6 with 11, provided 7 as the major product, after careful optimization of the conditions.

Products Formed in the Iodination of Compound 6

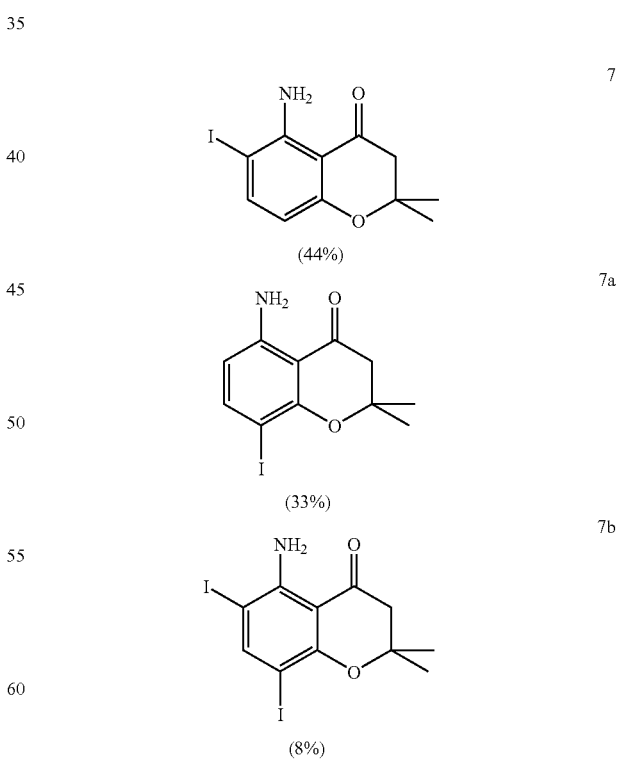

We have prepared compound 11 by employing two different methods, one according to a procedure developed by Tour et al.,[11] and the other according to a procedure developed by Kajisori et al.[12] We prefer the latter method, because we found Tour's method difficult to reproduce.

Scheme 12. Preparation of benzyltriethylammonium dichloroiodate (11)

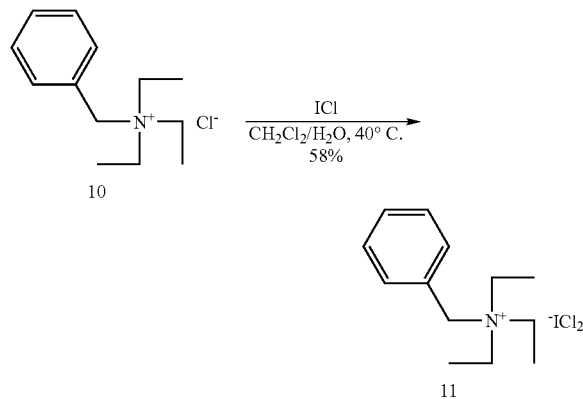

A suitably-protected coupling partner representing the FC-101 side chain (13) is made in two steps from commercially available N-(tert-butoxycarbonyl)-3-iodo-D-alanine methyl ester (12, Scheme 13). DIBAL reduction of this methyl ester to a primary alcohol and subsequent acetylation of the alcohol provides compound 13.

The two main fragments (7 and 13) are next coupled together using a palladium-catalyzed carbonylative cross-coupling to give the protected fusarochromanone (8, Scheme 10). We have reproducibly synthesized compound 8, employing a generic procedure developed by Jackson et al.,[13] This procedure involves in situ conversion of compound 13 to an organozinc intermediate that serves as the nucleophile in the cross-coupling reaction. This compound is transformed to the target product (1) after two deprotection steps. The first deprotection involves treatment of 8 with ammonia in methanol to remove the acetate group, providing 9, followed by removal of the t-Boc protecting group with trifluoroacetic acid (50% in acetic acid) to give 1. To date, this final reaction has been performed only on an analytical scale, and the formation of (1) has been confirmed by high resolution mass spectrometry.

Scheme 13: Preparation of a Suitably Protected Iodozinc Coupling Partner (13)

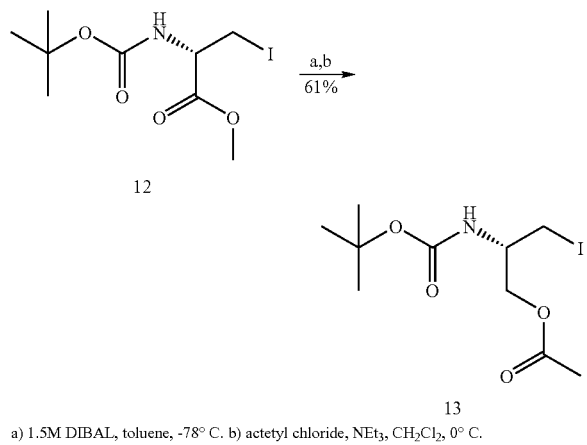

a) 1.5M DIBAL, toluene, -78° C. b) acetetyl chloride, NEt₃, CH₂Cl₂, 0° C.

Example 2

Preparation of 6-Hydroxy-2,2-dimethyl-chroman-4-one (3)

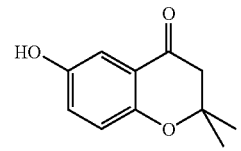

To a 250 mL, 2-necked round bottom flask equipped with a magnetic stir bar and a water-jacketed condenser capped with a balloon was added 2',5'-dihydroxyacetophenone (2, 8.00 g, 52.6 mmol), reagent grade acetone (19.45 mL, 263 mmol), piperidine (5.2 mL, 52.6 mmol) and freshly distilled pyridine (50 mL). The mixture was heated to a vigorous reflux with stirring under a nitrogen atmosphere for 2 d. The solvent was evaporated and the concentrate was dried under high vacuum. Reagent grade acetone (19.45 mL, 263 mmol), piperidine (5.2 mL, 52.6 mmol) and freshly distilled pyridine (50 mL) were added, and vigorous reflux with stirring under a nitrogen atmosphere was continued for 2d more. The solvent was evaporated, ethyl acetate (30 mL) and 30% aqueous $CuSO_4$ (30 mL) were added to the concentrate. The organic phase was washed with brine (1×30 mL), dried over $MgSO_4$, filtered, concentrated and dried under high vacuum. The dry crude product was passed through a silica gel column using 2:1 hexanes/ethyl acetate as eluent (Rf=0.3). The product gives off a purple color on an analytical silica gel plate illuminated with a short wave UV lamp. The fractions containing the pure product were transferred to a pre-weighed flask, the solvent was evaporated and the concentrate was dried under high vacuum. The reaction furnished 7.65 g of 3 (76%) as a brown solid. $^1H$ NMR (300 MHZ, $CDCl_3$): δ 7.32 (m, 1H), 7.04 (m, 1H), 6.82 (m, 1H), 5.48 (bs, 1H), 2.68 (s, 2H), 1.42 (s, 6H). $^{13}C$ NMR (75.5 MHZ, $CDCl_3$): δ 193.8, 154.4, 149.9, 125.2, 120.0, 119.6, 110.7, 79.0, 48.7, 26.5; HRMS ($EI^+$): calculated for $C_{11}H_{12}O_3$ [$M^+$] m/z 192.0786, found 192.0788.

Example 3

Preparation of 6-hydroxy-2,2-dimethyl-5-nitro-chroman-4-one (4)

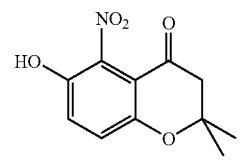

To a 250 mL round bottom flask equipped with a magnetic stir bar was added 3 (810 mg, 4.2 mmol) and 15 mL of glacial acetic acid. The mixture was stirred at room temperature until all of the solid dissolved. To a 25 mL vial was added $KNO_3$ (469 mg, 4.6 mmol) and just enough distilled water to dissolve all the $KNO_3$. The aqueous $KNO_3$ solution was transferred to the reaction flask with a pipet. The reaction flask was lowered into an ice water bath (~10° C.). Concentrated $H_2SO_4$ (1 mL) was added drop-wise. The mixture was stirred until all starting material was consumed, as monitored by TLC analysis. Ethyl acetate (20 mL) was added, and the biphasic mixture was transferred into a 500 mL separatory funnel. Saturated aqueous $Na_2CO_3$ was added cautiously until the aqueous layer was pH~7. The aqueous phase was extracted in ethyl acetate (3×20 mL), the combined organic phases were washed with brine (1×50 mL), dried over MgSO4, filtered, concentrated and dried under high vacuum. The dry crude product was passed through a silica gel column using 25:1 $CH_2Cl/EtOAc$ as eluent (Rf=0.3). The product gives off a red color on an analytical silica gel plate illuminated with a shortwave UV lamp. The fractions containing the pure product were transferred to a pre-weighed flask, the solvent was evaporated and the concentrate was dried under high vacuum. The reaction furnished 715 mg (72%) of 4 as a yellow solid. $^1$H NMR (300 MHZ, $CDCl_3$): δ 7.70 (bs, 1H), 7.21 (d, J=9 Hz, 1H), 7.04 (d, J=9 Hz, 1H), 2.76 (s, 2H), 1.46 (s, 6H). $^{13}$C NMR (75.5 MHZ, $CDCl_3$): δ 188.9, 154.4, 145.0, 126.4, 124.7(2), 113.1, 80.6, 49.0, 26.4; HRMS (EI$^+$): calculated for $C_{11}H_{11}NO_5[M^+]$ m/z 237.0637, found 237.0633.

Example 4

Preparation of trifluromethanesulfonic Acid 2,2-dimethyl-5-nitro-4-oxo-chroman-6-yl Ester (5)

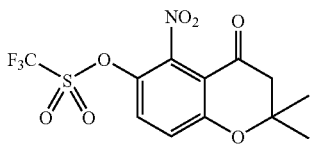

5

To a 100 mL, 2-necked round bottom flask equipped with a magnetic stir bar containing 4 (371 mg, 1.6 mmol) was added 10 mL of freshly distilled $CH_2Cl_2$. The mixture was stirred at room temperature under a nitrogen atmosphere until all solid was dissolved in solution. The reaction mixture was cooled in a water/ice bath, and freshly distilled triethylamine (654 mL, 4.7 mmol) was added via syringe. This was followed by the slow addition of trifluoromethanesulfonic anhydride (454 mL, 1.9 mmol). Stirring at 0° C. was continued until 4 was completely consumed, as determined by TLC analysis. The reaction was quenched with aqueous sodium bicarbonate (10 mL). The organic phase was washed with brine (1×0 mL), dried over MgSO$_4$, filtered, concentrated and dried under high vacuum. The crude product was passed through a silica gel column using $CH_2Cl_2$/hexanes (2:1) as the eluent (R$_f$=0.5). The reaction yielded 537 mg (93%) of 5 as a pale yellow solid. $^1$H NMR (300 MHZ, $CDCl_3$): δ7.54 (d, J=9 Hz, 1H), 7.15 (d, J=9 Hz, 1H), 2.79 (s, 2H), 1.50 (s, 6H); $^{13}$C NMR (75.5 MHZ, $CDCl_3$): δ 187.6, 159.2, 133.4, 129.1, 122.3, 120.7, 116.4, 112.1, 81.7, 48.5, 26.6; HRMS (EI$^+$): calculated for $C_{12}H_{10}F_3NO_7S$ [M$^+$] m/z 369.0130, found 369.0135.

Example 5

Preparation of 5-amino-2,2-dimethyl-chroman-4-one (6)

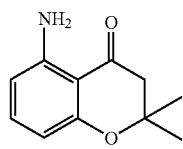

6

To an oven-dried hydrogenation flask was added 10% Pd—C (50 mg). The flask was attached to a Parr hydrogenation apparatus, evacuated with a water aspirator, pressurized with H$_2$ to 50 psi, and shaken at room temperature for 30 min to pre-activate the Pd catalyst. Following this preactivation period, the hydrogenation flask was cautiously detached from the apparatus, and a solution of 5 (546 mg, 1.48 mmol) in absolute ethanol (15 mL) and transferred to the flask with a pipette. Freshly distilled triethylamine (207 mL, 1.48 mmol) was also added to neutralize the HI produced during the course of the deiodination. The hydrogenation flask was again evacuated and pressurized with H$_2$ to 50 psi. Shaking of the flask was continued until all of the starting material was consumed (ca. 24 hr) as determined by TLC analysis. The reaction mixture was then filtered through a fritted glass filter funnel layered with Celite to remove the catalyst, and the filtrate was concentrated. Ethyl acetate (25 mL) was added to the concentrate, and the solution was washed with brine (1×25 mL), dried over MgSO$_4$, filtered, and concentrated to dryness. The crude product was passed through a short silica gel column using pure $CH_2Cl_2$ as the eluent (R$_f$=0.2). The reaction provided 235 mg (84%) of 6 as a yellow solid. $^1$H NMR (300 MHZ, $CDCl_3$): δ 7.11 (t, J=8 Hz, 1H), 6.28 (bs, 1H), 6.11 (m, 2H), 2.65 (s, 2H), 1.41 (s, 6H); $^{13}$C NMR (75.5 MHZ, $CDCl_3$): δ 194.8, 160.7, 150.8, 136.6, 107.6, 105.9, 104.4, 72.5, 49.4, 26.6); HRMS (EI$^+$): calculated for $C_{11}H_{13}NO_2$ [M$^+$] m/z 191.0496, found 191.0496.

Example 6

Preparation of 5-amino-6-iodo-2,2-dimethyl-chroman-4-one (7)

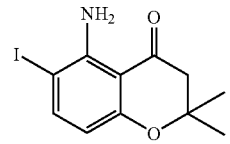

7

To a 100 mL round bottom flask equipped with a magnetic stir bar was added 6 (234 mg, 1.23 mmol), benzyltriethylammonium dichloroiodate (11, 480 mg, 1.23 mmol), sodium bicarbonate (113 mg, 1.35 mmol), $CH_2Cl_2$ (5 mL) and reagent grade methanol (2 mL). The flask was equipped with a water condenser, and the mixture was heated to 40° C. with stirring until all of compound 6 was consumed, as determined by TLC analysis. $CH_2Cl_2$ (10 mL) and 10% aqueous sodium bisulfite (10 ml) were added, the organic phase was washed with brine (1×10 mL), dried over MgSO$_4$, filtered, concentrated and dried under high vacuum. The dry, crude product was passed through a silica gel column using straight $CH_2Cl_2$ (Rf=0.5) as eluent. The reaction provided 171 mg (44%) of 7 as a yellow solid. $^1$H NMR (300 MHZ, $CDCl_3$): δ 7.58 (d, J=9 Hz, 1H), 6.00 (d, J=9 Hz, 1H), 2.67 (s, 2H), 1.40 (s, 6H). $^{13}$C NMR (75.5 MHZ, $CDCl_3$): δ 193.9, 161.3, 149.6, 145.4, 106.9, 105.8, 78.2, 73.6, 48.8, 26.5. HRMS (EI$^+$): calculated for $C_{11}H_{12}INO_2$ [M$^+$] m/z 316.9913, found 316.9906.

Two byproducts of this reaction are 5-amino-8-iodo-2,2-dimethyl-chroman-4-one (compound 7a, 33% yield, regioisomer) and 5-amino-6,8-diiodo-2,2-dimethyl-chroman-4-one (compound 7b, 8% yield, diiodinated byproduct). The regioisomer, 7a, is more polar, while the diiodinated species is less polar than compound 7, with 0.3 and 0.8 R$_f$ respectively in pure $CH_2Cl_2$. All three compounds may be reduced back to compound 6 by catalytic hydrogenation. Using a solvent ratio of $CH_2Cl/MeOH$ (1:1) in the reaction increases the yield of the diiodinated byproduct, 7b. Using $CH_2Cl_2/MeOH/H_2O$ (10:5:2) increases the yield of 7a. Employing iodine chloride as iodinating reagent gives 7b as the major product (>80% yield), under a variety experimental conditions similar to those outlined above.

Example 7

Preparation of (R)-acetic Acid 4-(5-amino-2,2-dimethyl-4-oxo-chroman-6-yl)-2-tert-butoxy-carbonylamino-4-oxo-butyl Ester (8)

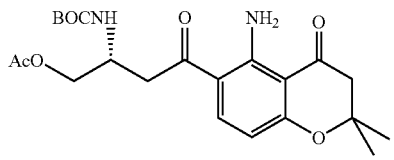

Zinc powder (144 mg, 2.2 mmol) was added to an oven-dried, nitrogen-flushed, 25 mL, 2-necked round bottom flask equipped with a water condenser and a magnetic stir bar. The set-up was evacuated under high vacuum for 30 min then flushed with nitrogen and capped with a nitrogen balloon. Freshly distilled THF (0.5 mL) and 1,2-dibromoethane (9 mL, 0.11 mmol) were added with a syringe. The slurry was heated to 60° C. intermittently with vigorous stirring over the course of 30 min. The mixture was cooled to room temperature and freshly distilled TMSCl (3 mL, 0.022 mmol) was added with a syringe. The mixture was stirred at 35° C. for 15 min then cooled to room temperature. Compound 13 (150 mg, 0.44 mmol), dissolved in freshly distilled THF (0.5 mL) was cannulated into the reaction mixture and the resulting mixture was heated to 45° C. with vigorous stirring until compound 13 is all consumed, as determined by TLC analysis using 4:1 hexanes/ethyl acetate as eluent. Compound 7 (97 mg, 0.31 mmol) and Pd(PPh$_3$)$_4$ (57 mg, 0.05 mmol), dissolved in a minimum amount of freshly distilled THF, were cannulated into the reaction mixture. The nitrogen atmosphere was replaced with a carbon monoxide atmosphere and the reaction mixture was heated at 45° C. for 3 d. Aqueous 10% NH$_4$Cl (8 mL) and ethyl acetate (10 mL) were added, the organic phase was washed with brine (1×10 mL), dried over MgSO$_4$, concentrated, filtered, and dried under high vacuum. The dry, crude product was passed though a silica gel column using 25:1 CH$_2$Cl$_2$/ethyl acetate as eluent (Rf=0.3). The compound gives off a purple color on an analytical silica gel plate illuminated with a short wave UV lamp. The reaction yielded 15 mg (11%) of 9 as a yellow solid. Unreacted starting material (compound 7, 70 mg) was recovered. The yield of 8 based on recovered (unreacted) starting material (7) was 21%. $^1$H NMR (300 MHZ, CDCl$_3$): δ 9.52 (bs, 1H), 9.39 (bs, 1H), 7.78 (d, J=9 Hz, 1H), 6.05 (d, J=9 Hz, 1H), 5.25 (bs, 1H), 4.28 (m, 2H), 4.13 (m, 1H), 3.17 (m, 1H), 3.03 (m, 1H), 2.68 (s, 2H), 2.04 (s, 3H), 1.44 (s, 6H), 1.41 (s, 9H); $^{13}$C NMR (75.5 MHZ, CDCl$_3$): δ 193.7(2), 170.9, 166.1, 155.3, 154.8, 140.0, 111.5, 104.5, 104.1, 79.4, 65.6, 51.6, 48.9, 39.7, 28.3, 26.5, 20.8; MS(ES$^+$): 435 [M+H]$^+$.

Example 8

Preparation of (R)-[3-(5-amino-2,2-dimethyl-4-oxo-chroman-6-yl)-1-hydroxymethyl-3-oxo-propyl]-carbamic Acid tert-butyl Ester (9)

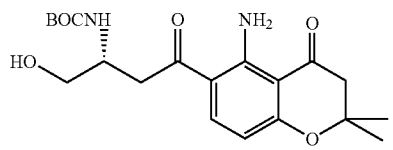

Method 1. To a round-bottom flask equipped with a magnetic stir bar and compound 8 (5 mg, 0.012 mmol) was added THF (1 mL) and distilled water (1 mL). Lithium hydroxide (2 mg, 0.048 mmol) was next added. The mixture was stirred at room temperature until all of the starting material was consumed, as determined by TLC (25:1 CH$_2$Cl$_2$/EtOAc). Ethyl acetate (5 mL) and water (2 mL) were added. The water phase was extracted in ethyl acetate (2×5 mL), and the combined organic extracts were washed with brine, dried over MgSO$_4$, filtered, and concentrated to dryness. The crude product was then dissolved in a minimum amount of methylene chloride and applied onto a preparative silica gel TLC plate. The plate was developed using CH$_2$Cl$_2$/EtOAc (1:1) as the eluent. The compound gives off a purple color on an analytical silica gel plate illuminated with a short wave UV lamp the way an authentic sample of FC-101 does. The reaction yielded 4 mg (89%) of 9 as a yellow solid.

Method 2. Reagent grade methanol (1 mL) was added to a 25 mL Erlenmeyer flask. The flask was placed in an ice bath and the solvent was bubbled with ammonia to saturation. The ammonia-saturated solvent was transferred with a syringe to a 10 mL round bottom flask containing 8. The mixture was stirred at room temperature until all of the starting material was consumed (as monitored by TLC). The solution was concentrated, and the concentrate was dried. The dry crude material was dissolved in a minimum amount of methylene chloride and applied onto a preparative silica gel TLC plate. The plate was developed using CH$_2$Cl$_2$/EtOAc (1:1) as the eluent. The reaction yielded 4 mg (89%) of 9 as a yellow solid. $^1$H NMR (300 MHZ, CDCl$_3$): δ 9.56 (bs, 1H), 9.44 (bs, 1H), 7.90 (d, J=9 Hz, 1H), 6.07 (d, J=9 Hz, 1H), 5.26 (bs, 1H), 4.02 (m, 1H), 3.70 (m, 2H), 3.17 (m, 1H), 3.06 (m, 1H), 2.68 (s, 2H), 1.44 (s, 6H), 1.41 (s, 9H); $^{13}$C NMR (75.5 MHZ, CDCl$_3$): δ 198.8, 193.8, 166.3, 156.0, 154.9, 140.6, 111.6, 104.4 (2), 79.7, 79.5, 64.8, 50.1, 48.9, 40.1, 28.3, 26.5. MS(ES$^+$): [M+H]$^+$ 393.

Example 9

Preparation of (R)-5-amino-6-(3-amino-4-hydroxy-butyryl)-2,2-dimethyl-chroman-4-one (1)

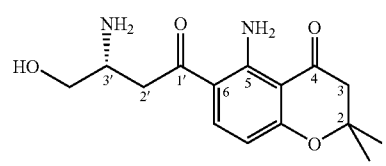

Fusarochromanone

To a round bottom flask containing an analytical amount of compound 9 was added 1 mL of a 1:1 solution of trifluoroacetic acid/glacial acetic acid. The solution was stirred at room temperature until all of the starting material was consumed, as determined by TLC (eluent: 1:1 CH$_2$Cl$_2$/EtOAc). The solvent was removed using a water aspirator. Aqueous ammonium hydroxide (1M, 0.5 mL) was added. Chloroform and methanol were added so that the solvent ratio was 5:2:1 chloroform/methanol/water. The extraction was repeated twice. The combined extracts were concentrated and dried. TLC analysis using 500:1 CH$_2$Cl$_2$/NH$_4$OH as eluent showed two spots, one with Rf=0.8 and the other with Rf=0.15, which is the Rf of an authentic sample of the natural product in the solvent system used. The compound gives off a bright light purple color on an analytical silica gel plate illuminated with a short wave UV lamp the way an authentic sample of FC-101 does. HRMS (EI$^+$): calculated for C$_{15}$H$_{20}$N$_2$O$_4$ [M+H]$^+$ 293.1501; found 293.1491.

Example 10

Synthesis of Benzyltriethylammonium Dichloroiodate (11)

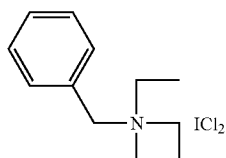

11

Commercially available benzyltriethylammonium chloride (10, 2.00 g, 8.79 mmol) was added to a clean 25 mL vial. This vial was capped and shaken until all of the solid dissolved. To a separate clean 25 mL vial was added iodine monochloride (834 mg, 5.126 mmol) and distilled $CH_2Cl_2$ (10 mL). The aqueous solution from the first vial was transferred to the second vial with a pipette. The resulting biphasic solution was tightly capped and shaken with a mechanical shaker for 1 h. The organic phase was extracted, dried over $MgSO_4$, filtered, and concentrated to dryness. No further purification was necessary. This reaction provided 1.98 g (58%) of 11 as an orange solid. $^1H$ NMR (300 MHZ, $CDCl_3$): δ 7.48 (m, 5H), 4.43 (s, 2H), 3.29 (m, 6H), 1.50 (m, 9H); $^{13}C$ NMR (75.5 MHZ, $CDCl_3$): δ 132.9, 131.3, 129.9, 126.0, 61.3, 53.1, 8.4.

Example 11

Preparation of (S)-acetic Acid 2-tert-butoxycarbonylamino-3-iodo-propyl Ester (13)

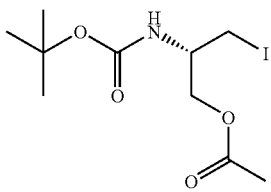

13

To an oven-dried, nitrogen-flushed, 50 ml, 2-necked round bottom flask equipped with a magnetic stir bar was added commercially available N-(tert-butoxycarbonyl)-3-iodo-D-alanine methyl ester (12, 658 mg, 2.0 mmol). The flask was evacuated under high vacuum for 30 min, flushed with nitrogen, and capped with a nitrogen balloon. It was then cooled in an isopropanol/dry ice bath (−78° C.). DIBAL (1.5 M in toluene, 16 mL, 24 mmol) was next added to the flask with a syringe. Stirring was continued until all of the starting material was consumed, as determined by TLC analysis (4:1 hexanes/ethyl acetate). The starting material gives off a red color on an analytical silica gel plate upon illumination with a short wave UV lamp. The mixture was cooled to 0° C. and then cautiously quenched with aqueous potassium tartrate (10 mL). The slurry was passed through a fritted glass filter funnel layered with celite. The organic phase was washed with brine (1×10 mL), dried over $MgSO_4$, filtered into a 50 mL round bottom flask equipped with a magnetic stir bar, concentrated and dried under high vacuum. The crude, dry intermediate is a colorless viscous oil. Methylene chloride (10 mL) was added into the flask, the mixture was stirred at room temperature until the oil was dissolved in a solution. The solution was lowered into an ice bath, acetic anhydride (378 mL, 4 mmol) and freshly distilled triethylamine (558 mL, 4 mmol) were added with a syringe, and stirring at 0° C. was continued until all starting material was consumed, as determined by TLC analysis. The reaction was quenched with aqueous sodium bicarbonate (10 mL). The organic phase was washed with brine (1×0 mL), dried over $MgSO_4$, filtered, concentrated and dried under high vacuum. The dry, crude product was passed through a silica gel column using 4:1 hexanes/ethyl acetate as eluent ($R_f$=0.4). The fractions containing the pure product were poured into a pre-weighed flask, the solvent was evaporated and the concentrate was dried under high vacuum. The two sequential reactions provided 13 as a colorless, viscous oil (415 mg, 61% overall). $^1H$ NMR (300 MHZ, $CDCl_3$): δ 4.82 (bd, J=8 Hz, 1H), 4.24 (m, 1H), 4.05 (m, 1H), 3.81 (m, 1H), 3.31 (m, 2H), 2.07 (s, 3H), 1.43 (s, 9H); $^{13}C$ NMR (75.5 MHZ, $CDCl_3$): δ 170.6, 154.8, 80.2, 65.3, 49.2, 28.3(3), 20.7, 7.5; MS($EI^+$): 344 $[M+H]^+$.

Example 12

Synthesis of FC-101 Alkyne Precursor

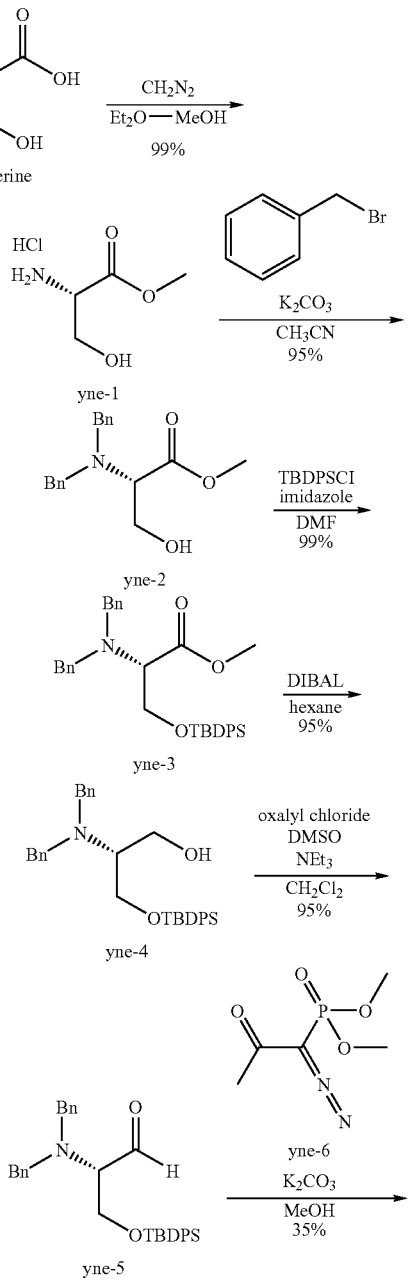

Scheme 14. Alkyne synthesis

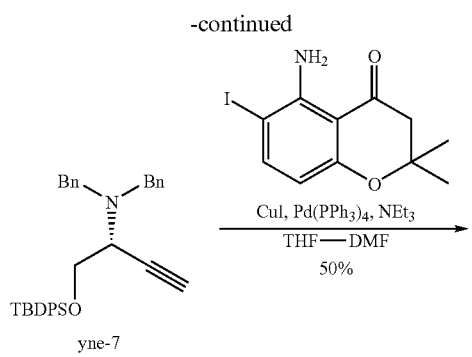

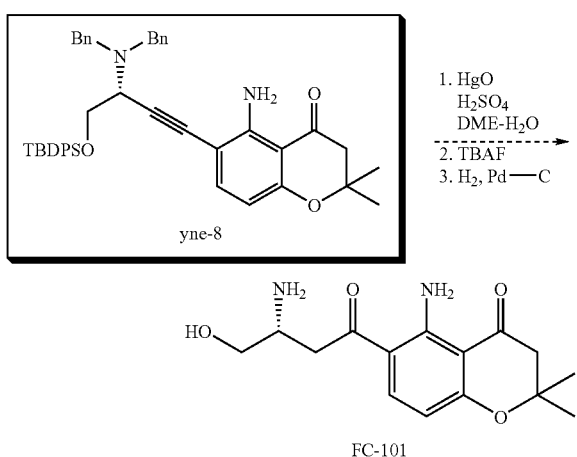

Compounds yne-2, yne-3, yne-4 and yne-5 were made following the procedure in Hulme, H. N. et al., *J. Chem. Soc. Perkin Trans.* 1, 2000, 1837-1841.

Example 13

Synthesis of Compound yne-1

(S)-2-Amino-3-hydroxy-propionic Acid Methyl Ester

To a round bottom flask equipped with a magnetic stir bar was added commercially available L-serine (25.00 g, 238 mmol). A minimum amount of reagent grade methanol was added to just dissolve the solid in solution. The flask was capped with a rubber septum. A solution of diazomethane in diethyl ether was added via a syringe at room temperature under a nitrogen atmosphere until all starting material has been consumed. The solvent was evaporated and the concentrate was dried under vacuum. The reaction yielded 28.00 g (235 mmol, 99%) of white solid. $^1$H-NMR (300 MHZ, D$_2$O): δ 4.13 (1H, t, J 3.8), 3.95 (1H, dd, J 12.7, 4.1), 3.83 (1H, dd, J 12.7, 3.5), 3.70 (3H, s). $^{13}$C-NMR (75.5 MHZ, D$_2$O): δ 169.1, 59.3, 54.8, 53.8. MS(ES$^+$): [M+H]$^+$120.

Example 14

Synthesis of Compound yne-6

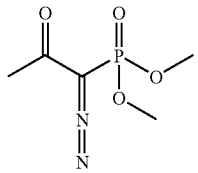

(1-Diazo-2-α-propyl)-phosphonic Acid Dimethyl Ester

To an N$_2$-flushed, oven-dried round bottom flask equipped with a magnetic stir bar was added sodium hydride (303 mg, 12.64 mmol). The flask was capped with a rubber septum and alternately evacuated and flushed with nitrogen. Freshly distilled THF (2 mL) was added via a syringe, and the mixture was stirred for 10 min at room temperature. THF (2 mL) and reagent grade benzene (5 mL) were added via a syringe, and the mixture was cooled to ~5-10° C. A solution of commercial (2-oxo-propyl)-phosphonic acid dimethyl ester (2000 mg, 12.04 mmol) in benzene (5 mL) was added via a syringe, and the resulting mixture was stirred under a nitrogen atmosphere for 1 h. A solution of toluenesulfonyl azide (2612 mg, 13.24 mmol) in benzene (5 mL) was added via a syringe. The solution was allowed to warm to room temperature and stirring under a nitrogen atmosphere was continued overnight. TLC analysis of the mixture, using straight ethyl acetate as eluent, revealed that all starting dimethyl ester has been consumed. The slurry was passed through a fritted filter funnel layered with celite. The residue was washed copiously with ethyl acetate. The eluate was washed with brine, dried over MgSO4, concentrated and dried under high vacuum. The dry crude was passed through a silica gel column using straight ethyl acetate as eluent. The reaction yielded 1700 mg (74%) of clear, yellow, viscous liquid. $^1$H-NMR (300 MHZ, CDCl$_3$): δ 3.75 (3H, s), 3.71 (3H, s), 2.14 (3H, s). $^{13}$C-NMR (75.5 MHZ, CDCl$_3$): δ 189.73, 53.44, 26.98. MS (ES$^+$): 193 [M+H]$^+$.

Example 15

Synthesis of Compound yne-7

(R)-Dibenzyl-[1-(tert-butyl-diphenyl-silanyloxymethyl)-prop-2-ynyl]-amine

To an N$_2$-flushed, oven-dried round bottom flask equipped with a magnetic stir bar was added aldehyde yne-5 (797 mg, 1.57 mmol), (1-diazo-2-oxopropyl)-phosphonic acid yne-6 (452 mg, 2.35 mmol), anhydrous potassium carbonate (434 mg, 3.14 mmol) and dry methanol (20 mL). The mixture was lowered into an ice bath. Stirring at 0° C. under a nitrogen atmosphere was commenced. The mixture was allowed to warm to room temperature and stirring continued overnight. TLC analysis using straight ethyl acetate as eluent revealed that all of the diazophosphonic acid methyl ester was consumed. Saturated ammonium chloride (10 mL) and ethyl acetate (20 mL) were added. The organic phase was separated and the water phase was extracted in ethyl acetate (3×10 mL). The combined organic phase was dried over MgSO$_4$, filtered, concentrated, and dried under high vacuum. The dry crude was passed through a silica gel column using 15:1 hexanes-ethyl acetate as eluent. The reaction yielded 277 mg (35%) of clear oil. $^1$H-NMR (300 MHZ, CDCl$_3$): δ 7.18-7.61 (20H, m), 3.85 (2H, d, J=13.9 Hz), 3.76-3.80 (1H, m), 3.68-3.72 (3H, m), 3.44 (2H, d, J=13.9 Hz), 1.00 (9H, s). $^{13}$C-NMR (75.5 MHZ, CDCl$_3$): δ 139.5, 135.6, 133.3, 129.6, 128.7, 128.2, 127.6, 126.9, 79.7, 73.6, 64.8, 55.2, 54.0, 26.7, 19.2. MS(ES$^+$): [M+H]$^+$ 504.2733 observed, 504.2723 calculated.

Example 16

Synthesis of Compound yne-8

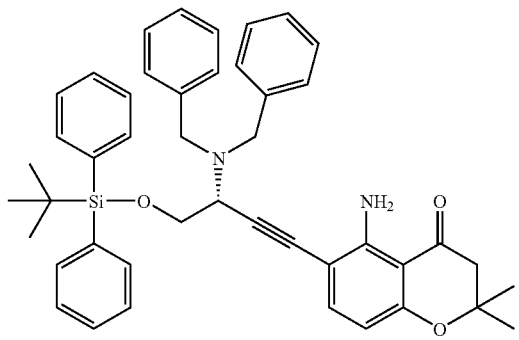

(R)-5-Amino-6-[4-(tert-butyl-diphenyl-silanyloxy)-3-dibenzylamino-but-1-ynyl]-2,2-dimethyl-chroman-4-one To an oven-dried, N$_2$-flushed round bottom flask equipped with a magnetic stir bar was added in succession alkyne yne-7 (75 mg, 0.15 mmol), then a solution of 5-amino-6-iodochromanone (44 mg, 0.138 mmol) in 2 mL of freshly distilled THF, then commercial copper iodide (2.6 mg, 0.0138 mmol), then palladium tetrakistriphenylphosphine (16 mg, 0.0138 mmol), then triethylamine (58 mL, 0.415 mmol), then 0.7 mL of dry DMF. The mixture was stirred at room temperature under a nitrogen atmosphere. After 4 hours TLC analysis using 12:1 hexanes-ethyl acetate revealed that all starting alkyne has been consumed. Water (2 mL) and methylene chloride (2 mL) were added. The organic phase was separated, and the water phase was extracted in methylene chloride (3×2 mL). The combined organic phase was washed with brine, dried over MgSO4, filtered, concentrated and dried under high vacuum. The dry crude was passed through a silica gel column using 12:1 hexanes-ethyl acetate as eluent. The reaction yielded 47 mg (46%) of yellow viscous oil. 1H-NMR (300 MHZ, CDCl$_3$): δ 7.59 (1H, d, J=8.4 Hz), 7.21-7.61 (20H, m), 6.10 (1H, d, J=8.4 Hz), 3.81-3.99 (5H, m), 3.52 (2H, d, J 8.4), 2.68 (2H, s), 1.43 (6H, s), 1.03 (9H, s). $^{13}$C-NMR (75.5 MHZ, CDCl$_3$): δ 194.3, 161.0, 151.5, 139.5, 135.6, 133.2, 129.6, 128.7, 128.3, 127.7, 126.9, 104.7, 104.4, 100.5, 90.7, 81.4, 78.4, 65.4, 55.6, 55.0, 49.2, 26.8, 26.6, 19.2. MS(ES$^+$): [M+H]$^+$ 693.3524 observed, 693.3512 calculated.

Example 17

Synthesis of FC-101 Alkene Precursor

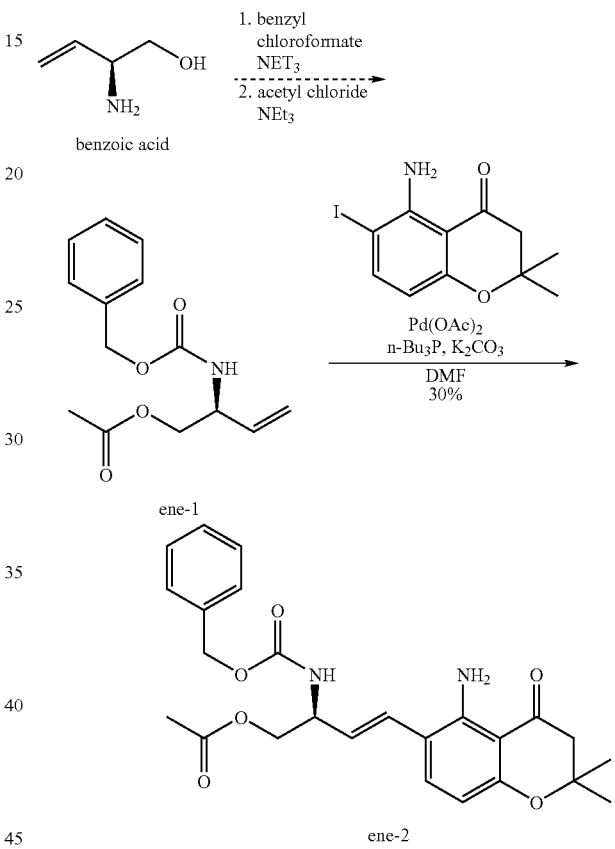

Synthesis of Compound ene-2

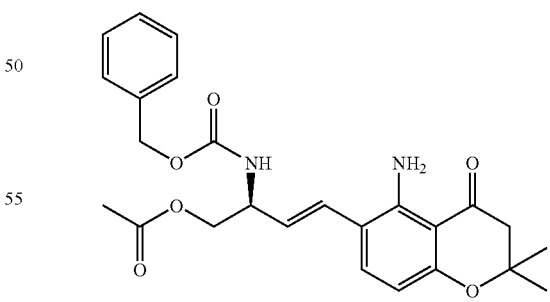

Acetic Acid 4-(5-amino-2,2-dimethyl-4-oxo-chroman-6-yl)-2-benzyloxycarbonylamino-but-3-enyl Ester To an oven-dried, N$_2$-flushed, 2-necked round bottom flask equipped with a reflux condenser and a magnetic stir bar was added vinyl glycine ene-1 (76 mg, 0.29 mmol), anhydrous potassium carbonate (44 mg, 0.32 mmol), palladium acetate (6.5 mg, 0.029 mmol), tri-n-butylphosphine (14.5 mL, 0.058 mmol) and 1 mL of dry DMF. A solution of 5-amino-6-iodochromanone (100 mg, 0.32 mmol) in 1 mL of dry DMF was added via a syringe. The mixture was heated to 80° C. with stirring under a nitrogen atmosphere for 2 d. TLC analysis of the reaction mixture using 8.5:1 methylene chloride-ethyl acetate as eluent revealed that all of the starting ene-1 has been consumed. Brine (2 mL) and ethyl acetate (2 mL) were added. The organic phase was separated, and the water phase was extracted in ethyl acetate (3×2 mL). The combined organic phase was washed with brine, dried over $MgSO_4$, filtered, concentrated and dried under high vacuum. The dry crude was passed through a silica gel column using 8.5:1 methylene chloride-ethyl acetate as eluent. The reaction yielded 38 mg (30%) of yellow solid. $^1$H-NMR (300 MHZ, $CDCl_3$) δ 7.36-7.32 (5H, m), 7.19 (1H, d, J=8.4 Hz), 6.58 (2H, bs), 6.49 (1H, d, J=15.4 Hz), 6.12 (1H, d, J=8.7 Hz), 5.81 (1H, dd, J 15.6, 6.3), 5.11 (2H, s), 5.18 (1H, d, J 8.1), 5.10 (2H, s), 4.61 (1H, bs), 4.27-4.14 (2H, m), 2.66 (2H, s), 2.03 (3H, s), 1.41 (6H, s). $MS(ES^+)$: $[M+H]^+$ 453.

DESCRIPTION OF THE RELATED ART

References cited throughout this specification are listed here by number and are incorporated herein by reference. The discussion of references herein is intended merely to summarize the assertions made by their authors and no admission is made that any reference constitutes prior art. Applicants reserve the right to challenge the accuracy and pertinence of the cited references:
1. Lee, Y.; Mirocha, C. J.; Schroeder, D. J.; Walser, M. M. *Appl. Environ. Microbiol.* 1985, 50, 102.
2. Minervini, F.; Lucivero, G.; Visconti, A.; Bottalico, C. *Natural Toxins,* 1992, 1, 15.
3. Nie, D. *Investigation of Calcification and Vascularization of the Epiphyseal Growth Plate Cartilage Using Avian Tibial Dyschondroplasia and Hypervitaminosis A as Models*; Ph.D. Thesis, Department of Chemistry and Biochemistry, University of South Carolina, Columbia, 1997.
4. Folkman, *J. Ann. Surg.* 1972, 175, 409-416.
5. Folkman, *J. Nat. Med.* 1995, 1, 27-31.
6. Pathre, S. V.; Gleason, W. B. *Can. J. Chem.* 1986, 64, 1308.
7. Pawlosky, R. J.; Mirocha, C. J. *Biol. Mass Spec.* 1991, 29, 743.
8. Wuthier, R. E. and Smith, M. D. (unpublished results).
9. Kabbe, H. J. *Synthesis,* 1978, 12, 886-887.
10. Sun, H. B.; Qing, F. L.; Chen, X. *Synthesis,* 1997, 11, 1249-1251.
11. Kosynkin, D. V.; Tour, J. M. *Org. Lett.,* 2001, 3(7), 991-992.
12. Kajisori, S,; Kakinami, T. Japanese Patent JP 87-123670 19870522.
13. a. Jackson, R. F. W.; Turner, D.; Block, M. H. *J. Chem. Soc., Chem. Commun.* 1995, 2207-2208. b. Jackson, R. F. W.; James, K;. Wythes, M. J.; Wood, A. *J. Chem. Soc., Chem. Commun.* 1989, 644-645. c. Jackson, R. F. W.; Turner, D.; Block, M. H. *J. Chem. Soc., Perkin Trans* 1, 1997, 865-870. d. Dexter, C. S.; Jackson, R. F. W.; Elliott, J. *Tetrahedron,* 2000, 56, 4539-4540. e. Dunn, M. J.; Jackson, R. F. W.; Pietruszka, J.; Wishart, N.; Ellis, D.; Wythes, M. J. *Synlett,* 1993, 499-500.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:
1. A chromanone corresponding to Formula 21:

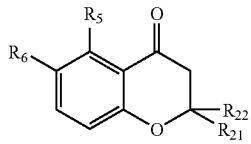

wherein
$R_5$ is amino or nitro;
$R_6$ is amino, hydroxy, halo, perfluorinated sulfonic ester, $R_{61}C(O)—$, $R_{62}C(O)O—$, $R_{61}C(O)NH—$, $R_{62}CHCH—$ or $R_{62}CC—$;
$R_{21}$ and $R_{22}$ are independently hydrogen, alkyl, or aryl;
$R_{61}$ is hydrogen, heterocyclo, alkoxy, heterocyclooxy, amino, or halo, and
$R_{62}$ is hydrogen, hydrocarbyl, substituted hydrocarbyl, heterocyclo, alkoxy, heterocyclooxy, amino, or halo.

2. The chromanone of claim 1 wherein $R_5$ is $—NO_2$.
3. The chromanone of claim 1 wherein $R_5$ is $—NH_2$.
4. The chromanone of claim 1 wherein $R_6$ is $—OH$.
5. The chromanone of claimi wherein $R_6$ is $R_{62}CHCH—$ or $R_{62}CC—$.
6. The chromanone of claim 2 wherein $R_6$ is $—OH$.
7. The chromanone of claim 2 wherein $R_6$ is perfluorinated sulfonic ester.
8. The chromanone of claim 5 wherein $R_5$ is $—NH_2$.
9. The chromanone of claim 8 wherein $R_{21}$ and $R_{22}$ are methyl.
10. The chromanone of claim 8 wherein $R_{62}$ is substituted hydrocarbyl.
11. A chromanone corresponding to Formula 62 or 67

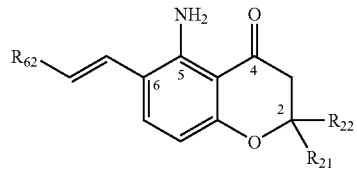

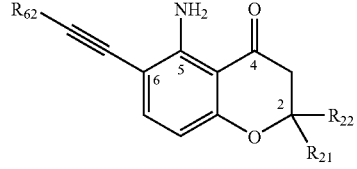

wherein
$R_{62}$ is hydrogen, hydrocarbyl, substituted hydrocarbyl, heterocyclo, alkoxy, heterocyclooxy, amino or halo; and
$R_{21}$ and $R_{22}$ are independently hydrogen, alkyl, or aryl.
12. The chromanone of claim 11 having the structure

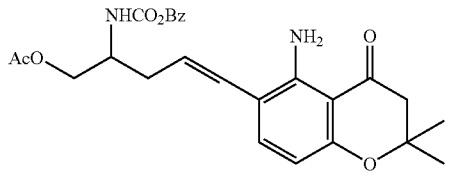

13. The chromanone of claim 11 having the structure

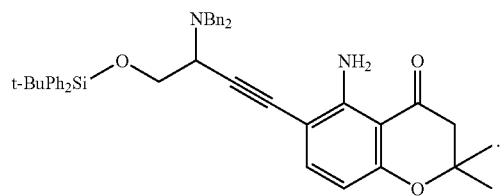

14. The chromanone of claim 11 corresponding to Formula 62.

15. The chromanone of claim 11 corresponding to Formula 67.

16. The chromanone of claim 14 wherein $R_{62}$ is substituted alkyl and $R_{21}$ and $R_{22}$ are independently hydrogen or alkyl.

17. The chromanone of claim 15 wherein $R_{62}$ is substituted alkyl and $R_{21}$ and $R_{22}$ are independently hydrogen or alkyl.

\* \* \* \* \*